(12) United States Patent
Frost et al.

(10) Patent No.: US 11,547,590 B2
(45) Date of Patent: Jan. 10, 2023

(54) ORTHOPEDIC DEVICE HAVING A SUSPENSION ELEMENT

(71) Applicant: OSSUR ICELAND EHF, Reykjavik (IS)

(72) Inventors: Lindsay Frost, Foothill Ranch, CA (US); Jane Price, Foothill Ranch, CA (US); Patrick Kiruki, Foothill Ranch, CA (US); Jared Olivo, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 658 days.

(21) Appl. No.: 16/201,370

(22) Filed: Nov. 27, 2018

(65) Prior Publication Data
US 2019/0159922 A1 May 30, 2019

Related U.S. Application Data

(60) Provisional application No. 62/590,944, filed on Nov. 27, 2017.

(51) Int. Cl.
*A61F 5/01* (2006.01)

(52) U.S. Cl.
CPC .......... *A61F 5/0125* (2013.01); *A61F 5/0123* (2013.01); *A61F 5/0109* (2013.01); *A61F 2005/0172* (2013.01); *A61F 2005/0176* (2013.01); *A61F 2005/0179* (2013.01); *A61F 2005/0197* (2013.01)

(58) Field of Classification Search
CPC .... A61F 5/0123; A61F 5/0125; A61F 5/0109; A61F 2005/0172; A61F 2005/0176; A61F 2005/0179; A61F 2005/0197; A61F 5/05; A61F 5/058; A61F 5/05825; A61F 5/05841; A61F 5/0585
See application file for complete search history.

(56) References Cited

U.S. PATENT DOCUMENTS

| | | | |
|---|---|---|---|
| 73,768 | A | 1/1868 | Allen |
| 1,601,659 | A | 9/1926 | Van Harlingen |
| 2,195,024 | A | 3/1940 | Bullock |
| 2,467,907 | A | 4/1949 | Peckham |
| 2,536,454 | A | 1/1951 | McIntyre |
| 2,558,986 | A | 7/1951 | Seelert |

(Continued)

FOREIGN PATENT DOCUMENTS

| | | |
|---|---|---|
| DE | 33 20 274 A1 | 12/1984 |
| DE | 196 31 632 A1 | 2/1998 |

(Continued)

OTHER PUBLICATIONS

International Search Report from PCT Application No. PCT/US2018/062561, dated Mar. 14, 2019.

(Continued)

*Primary Examiner* — Camtu T Nguyen
(74) *Attorney, Agent, or Firm* — Workman Nydegger

(57) ABSTRACT

An orthopedic device includes a frame, a brace component, and a suspension element supporting the brace component and connecting the brace component to the frame. The suspension element is suspended relative to the frame and capable of independent movement relative thereto in a controlled manner.

13 Claims, 8 Drawing Sheets

(56) References Cited

U.S. PATENT DOCUMENTS

| | | |
|---|---|---|
| 2,959,168 A | 11/1960 | Shook |
| 3,316,900 A | 5/1967 | Young |
| 3,348,812 A | 10/1967 | Story |
| 3,444,560 A | 5/1969 | Northup, Jr. |
| 3,753,625 A | 8/1973 | Fabrizio et al. |
| 3,947,156 A | 3/1976 | Becker |
| 3,976,057 A | 8/1976 | Barclay |
| 4,064,569 A | 12/1977 | Campbell |
| 4,088,130 A | 5/1978 | Applegate |
| 4,100,918 A | 7/1978 | Glancy |
| 4,145,766 A | 3/1979 | May |
| 4,220,148 A | 9/1980 | Lehneis |
| 4,298,992 A | 11/1981 | Burnstein et al. |
| 4,320,747 A | 3/1982 | Daniell, Jr. |
| 4,340,041 A | 7/1982 | Frank |
| 4,361,142 A | 11/1982 | Lewis et al. |
| 4,370,977 A | 2/1983 | Mauldin et al. |
| 4,372,298 A | 2/1983 | Lerman |
| 4,397,308 A | 8/1983 | Hepburn |
| 4,407,276 A | 10/1983 | Bledsoe |
| 4,428,369 A | 1/1984 | Peckham et al. |
| 4,433,679 A | 2/1984 | Mauldin et al. |
| 4,463,751 A | 8/1984 | Bledsoe |
| 4,489,718 A | 12/1984 | Martin |
| 4,506,661 A | 3/1985 | Foster |
| 4,508,111 A | 4/1985 | Hepburn |
| 4,520,802 A | 6/1985 | Mercer et al. |
| 4,523,585 A | 6/1985 | Lamb et al. |
| 4,649,906 A | 3/1987 | Spademan |
| 4,655,201 A | 4/1987 | Pirmantgen |
| 4,657,000 A | 4/1987 | Hepburn |
| 4,691,694 A | 9/1987 | Boyd et al. |
| 4,697,583 A | 10/1987 | Mason et al. |
| 4,723,539 A | 2/1988 | Townsend |
| 4,732,143 A | 3/1988 | Kausek et al. |
| 4,733,656 A | 3/1988 | Marquette |
| 4,768,762 A | 9/1988 | Lund |
| 4,773,404 A | 9/1988 | Townsend |
| 4,790,299 A | 12/1988 | Marquette |
| 4,793,333 A | 12/1988 | Marquette |
| 4,817,588 A | 4/1989 | Bledsoe |
| 4,856,500 A | 8/1989 | Spademan |
| 4,856,501 A | 8/1989 | Castillo et al. |
| 4,865,024 A | 9/1989 | Hensley et al. |
| 4,884,760 A | 12/1989 | Baggio et al. |
| 4,890,607 A | 1/1990 | Townsend |
| 4,911,709 A | 3/1990 | Marlow et al. |
| 4,955,369 A | 9/1990 | Bledsoe et al. |
| 4,961,416 A | 10/1990 | Moore et al. |
| 4,966,133 A | 10/1990 | Kausek |
| 4,982,732 A | 1/1991 | Morris |
| 4,991,571 A | 2/1991 | Kausek |
| 5,002,045 A | 3/1991 | Spademan |
| 5,018,514 A | 5/1991 | Grood et al. |
| 5,020,797 A | 6/1991 | Burns |
| 5,038,765 A | 8/1991 | Young et al. |
| 5,052,375 A | 10/1991 | Stark et al. |
| 5,063,917 A | 11/1991 | Young et al. |
| 5,176,622 A | 1/1993 | Anderson et al. |
| 5,213,094 A | 5/1993 | Bonutti |
| 5,230,696 A | 7/1993 | Silver et al. |
| 5,230,697 A | 7/1993 | Castillo et al. |
| 5,261,871 A | 11/1993 | Greenfield |
| 5,347,894 A | 9/1994 | Fischer |
| 5,357,654 A | 10/1994 | Hsing-Chi |
| 5,437,611 A | 8/1995 | Stern |
| 5,443,444 A | 8/1995 | Pruyssers |
| 5,452,475 A * | 9/1995 | Hunt, Jr. ............ A63B 71/1225 2/22 |
| 5,456,268 A | 10/1995 | Bonutti |
| 5,472,410 A | 12/1995 | Hamersly |
| 5,472,412 A | 12/1995 | Knoth |
| 5,514,082 A | 5/1996 | Smith, III |
| 5,575,764 A | 11/1996 | Van Dyne |
| 5,588,956 A | 12/1996 | Billotti |
| 5,599,288 A | 2/1997 | Shirley et al. |
| 5,624,390 A | 4/1997 | Van Dyne |
| 5,628,722 A | 5/1997 | Solomonow et al. |
| 5,658,241 A | 8/1997 | Deharde et al. |
| 5,662,596 A | 9/1997 | Young |
| 5,683,353 A | 11/1997 | Hamersly |
| 5,685,830 A | 11/1997 | Bonutti |
| 5,807,294 A | 9/1998 | Cawley et al. |
| 5,827,208 A | 10/1998 | Mason et al. |
| 5,857,988 A | 1/1999 | Shirley |
| 5,873,847 A | 2/1999 | Bennett et al. |
| 5,891,061 A | 4/1999 | Kaiser |
| 5,891,071 A | 4/1999 | Sterns et al. |
| 5,921,946 A | 7/1999 | Tillinghast et al. |
| 5,934,599 A | 8/1999 | Hammerslag |
| 5,950,245 A | 9/1999 | Binduga |
| 5,954,677 A | 9/1999 | Albrecht et al. |
| 5,997,493 A | 12/1999 | Young |
| 6,001,075 A | 12/1999 | Clemens et al. |
| 6,004,283 A | 12/1999 | Young |
| 6,074,355 A | 6/2000 | Bartlett |
| 6,110,137 A | 8/2000 | Bastyr et al. |
| 6,110,138 A | 8/2000 | Shirley |
| 6,129,690 A | 10/2000 | Hamlin et al. |
| RE37,209 E | 6/2001 | Hensley et al. |
| 6,245,034 B1 | 6/2001 | Bennett et al. |
| RE37,297 E | 7/2001 | Smith, III |
| 6,290,664 B1 | 9/2001 | Nauert |
| 6,331,169 B1 | 12/2001 | Bastyr et al. |
| 6,409,693 B1 | 6/2002 | Brannigan |
| 6,413,232 B1 | 7/2002 | Townsend et al. |
| 6,425,166 B1 | 7/2002 | Seligman et al. |
| 6,436,058 B1 | 8/2002 | Krahner et al. |
| 6,471,664 B1 | 10/2002 | Campbell et al. |
| 6,500,138 B1 | 12/2002 | Irby et al. |
| 6,551,264 B1 | 4/2003 | Cawley et al. |
| 6,666,837 B2 | 12/2003 | Weihermuller |
| 6,740,054 B2 | 5/2004 | Sterns |
| 6,752,775 B2 | 6/2004 | Seligman et al. |
| 6,834,752 B2 | 12/2004 | Irby et al. |
| 6,875,187 B2 | 4/2005 | Castillo |
| 6,936,020 B2 | 8/2005 | Davis |
| 6,993,808 B1 | 2/2006 | Bennett et al. |
| 7,004,919 B2 | 2/2006 | Gaylord et al. |
| 7,037,287 B2 | 5/2006 | Cormier et al. |
| 7,059,329 B2 | 6/2006 | Mason et al. |
| 7,074,201 B2 | 7/2006 | Reinecke et al. |
| 7,097,627 B2 | 8/2006 | Enzerink et al. |
| 7,117,569 B2 | 10/2006 | Bledsoe |
| 7,150,721 B2 | 12/2006 | Houser |
| 7,182,740 B1 | 2/2007 | Castillo |
| 7,192,407 B2 | 3/2007 | Seligman et al. |
| 7,198,610 B2 | 4/2007 | Ingimundarson et al. |
| 7,201,728 B2 | 4/2007 | Sterling |
| 7,207,960 B2 | 4/2007 | Kenney |
| 7,235,058 B2 | 6/2007 | Doty et al. |
| 7,235,059 B2 | 6/2007 | Mason et al. |
| 7,309,322 B2 | 12/2007 | Albrecht et al. |
| 7,311,687 B2 | 12/2007 | Hoffmeier et al. |
| D577,828 S | 9/2008 | Ingimundarson et al. |
| 7,431,708 B2 | 10/2008 | Sreeramagiri |
| 7,435,234 B2 | 10/2008 | Gamada |
| 7,485,103 B2 | 2/2009 | Mason et al. |
| 7,500,957 B2 | 3/2009 | Bledsoe |
| 7,534,217 B2 | 5/2009 | Seligman et al. |
| 7,534,219 B2 | 5/2009 | Sterns |
| 7,544,174 B2 | 6/2009 | Nathanson |
| 7,553,289 B2 | 6/2009 | Cadichon |
| 7,597,675 B2 | 10/2009 | Ingimundarson et al. |
| 7,662,122 B2 | 2/2010 | Sterling |
| 7,722,555 B2 | 5/2010 | Doty et al. |
| 7,727,174 B2 | 6/2010 | Chang et al. |
| 7,749,183 B2 | 7/2010 | Ingimundarson et al. |
| 7,757,303 B2 | 7/2010 | Miller |
| 7,806,842 B2 | 10/2010 | Stevenson et al. |
| 7,811,242 B2 | 10/2010 | Seligman |
| 7,846,115 B2 | 12/2010 | Seligman et al. |
| 7,850,632 B2 | 12/2010 | Gilmour |

(56) References Cited

U.S. PATENT DOCUMENTS

| | | | |
|---|---|---|---|
| 7,905,851 B1 * | 3/2011 | Bledsoe | A61F 5/0123 |
| | | | 128/95.1 |
| 7,927,299 B2 | 4/2011 | Krause | |
| 7,963,933 B2 | 6/2011 | Nace | |
| 3,048,013 A1 | 11/2011 | Ingimundarson et al. | |
| 8,128,587 B2 | 3/2012 | Stevenson et al. | |
| 8,376,974 B2 | 2/2013 | Nace | |
| 8,882,688 B1 | 11/2014 | Ancinec | |
| 8,920,350 B2 | 12/2014 | Merkley et al. | |
| 9,220,624 B2 | 12/2015 | Jansson et al. | |
| 9,539,135 B2 | 1/2017 | Romo et al. | |
| 2002/0013544 A1 | 1/2002 | Sterns | |
| 2002/0052568 A1 | 5/2002 | Houser et al. | |
| 2002/0052663 A1 | 5/2002 | Herr et al. | |
| 2002/0133108 A1 | 9/2002 | Jagodzinski | |
| 2004/0002674 A1 | 1/2004 | Sterling | |
| 2004/0030411 A1 | 2/2004 | Caspers | |
| 2004/0049140 A1 | 3/2004 | Doty et al. | |
| 2004/0049290 A1 | 3/2004 | Bedard | |
| 2004/0054307 A1 | 3/2004 | Mason et al. | |
| 2004/0054311 A1 | 3/2004 | Sterling | |
| 2004/0068215 A1 | 4/2004 | Adelson et al. | |
| 2004/0097859 A1 | 5/2004 | Sterns | |
| 2005/0015156 A1 | 1/2005 | Hikichi | |
| 2005/0020951 A1 | 1/2005 | Gaylord et al. | |
| 2005/0177082 A1 | 8/2005 | Bledsoe | |
| 2005/0245853 A1 | 11/2005 | Scorvo | |
| 2005/0273025 A1 | 12/2005 | Houser | |
| 2006/0100560 A1 | 5/2006 | Gilmour | |
| 2006/0100561 A1 | 5/2006 | Gilmour | |
| 2006/0116616 A1 | 6/2006 | Albrecht et al. | |
| 2006/0135902 A1 | 6/2006 | Ingimundarson et al. | |
| 2006/0142680 A1 | 6/2006 | Iarocci | |
| 2007/0010772 A1 | 1/2007 | Ryan | |
| 2007/0050044 A1 | 3/2007 | Haynes et al. | |
| 2007/0100265 A1 | 5/2007 | Gamada | |
| 2007/0232972 A1 | 10/2007 | Martinez | |
| 2007/0270976 A1 | 11/2007 | Deharde et al. | |
| 2008/0051684 A1 | 2/2008 | Gamada | |
| 2008/0066272 A1 | 3/2008 | Hammerslag et al. | |
| 2008/0195013 A1 | 8/2008 | Ingimundarson et al. | |
| 2008/0200856 A1 | 8/2008 | Cadichon | |
| 2008/0222766 A1 * | 9/2008 | Arensdorf | A41D 1/08 |
| | | | 2/22 |
| 2008/0249448 A1 | 10/2008 | Stevenson et al. | |
| 2008/0294079 A1 | 11/2008 | Sterling et al. | |
| 2009/0054819 A1 | 2/2009 | Einarsson | |
| 2009/0076426 A1 | 3/2009 | Einarsson et al. | |
| 2009/0099495 A1 | 4/2009 | Campos et al. | |
| 2009/0099562 A1 | 4/2009 | Ingimundarson et al. | |
| 2009/0105622 A1 | 4/2009 | Sterling et al. | |
| 2009/0124948 A1 | 5/2009 | Ingimundarson et al. | |
| 2009/0171469 A1 | 7/2009 | Thorsteinsson et al. | |
| 2009/0240181 A1 | 9/2009 | Sreeramagiri et al. | |
| 2009/0259154 A1 | 10/2009 | Nace | |
| 2009/0281637 A1 | 11/2009 | Martin | |
| 2009/0287128 A1 | 11/2009 | Ingimundarson et al. | |
| 2010/0010409 A1 | 1/2010 | Bejarano | |
| 2010/0056970 A1 | 3/2010 | Nace | |
| 2010/0162539 A1 | 7/2010 | Rancon | |
| 2011/0098618 A1 * | 4/2011 | Fleming | A61F 5/0123 |
| | | | 602/16 |
| 2011/0270413 A1 | 11/2011 | Haynes | |
| 2012/0022667 A1 | 1/2012 | Accinni et al. | |
| 2012/0046585 A1 | 2/2012 | Lee et al. | |
| 2012/0059296 A1 | 3/2012 | Kompa | |
| 2012/0157902 A1 | 6/2012 | Castillo et al. | |
| 2013/0110020 A1 | 5/2013 | Ingimundarson et al. | |
| 2013/0150761 A1 | 6/2013 | Romo et al. | |
| 2013/0172797 A1 | 7/2013 | Merkley et al. | |
| 2013/0178771 A1 | 7/2013 | Moir et al. | |
| 2013/0331754 A1 | 12/2013 | Dunn et al. | |
| 2014/0099189 A1 | 4/2014 | Morris et al. | |
| 2014/0213948 A1 * | 7/2014 | Romo | A61F 5/0125 |
| | | | 602/16 |
| 2014/0214016 A1 * | 7/2014 | Ingimundarson | A61F 5/0123 |
| | | | 606/16 |
| 2015/0005685 A1 | 1/2015 | Chetlapalli et al. | |
| 2015/0290014 A1 | 10/2015 | Anglada et al. | |
| 2016/0120683 A1 | 5/2016 | Romo et al. | |
| 2016/0151189 A1 | 6/2016 | Romo et al. | |
| 2016/0367391 A1 | 12/2016 | Paulos et al. | |

FOREIGN PATENT DOCUMENTS

| | | |
|---|---|---|
| DE | 196 45 076 A1 | 5/1998 |
| DE | 198 11 925 A1 | 10/1999 |
| DE | 10 259 751 A1 | 7/2004 |
| DE | 10 2010 006 089 A1 | 8/2010 |
| EP | 0 841 044 A1 | 5/1998 |
| EP | 0 941 722 A1 | 9/1999 |
| EP | 1 114 619 A1 | 7/2001 |
| EP | 1 302 184 A1 | 4/2003 |
| EP | 1 575 464 A1 | 9/2005 |
| EP | 1 880 802 A2 | 1/2008 |
| EP | 2 612 624 A1 | 7/2013 |
| FR | 2 122 846 A5 | 9/1972 |
| FR | 2 486 852 A1 | 1/1982 |
| FR | 2 663 380 A1 | 12/1991 |
| FR | 2 723 842 A1 | 3/1996 |
| FR | 2 777 489 A1 | 10/1999 |
| FR | 2 828 093 A1 | 2/2003 |
| GB | 1 213 855 A | 11/1970 |
| WO | 8501204 A1 | 3/1985 |
| WO | 86/04228 A1 | 7/1986 |
| WO | 9522700 A1 | 8/1995 |
| WO | 95/27451 A1 | 10/1995 |
| WO | 96/16615 A1 | 6/1996 |
| WO | 2004/056293 A1 | 7/2004 |
| WO | 2006/044423 A2 | 4/2006 |
| WO | 2009126724 A2 | 10/2009 |
| WO | 2010/087899 A2 | 8/2010 |

OTHER PUBLICATIONS

Defrate, Louis E., et al., "In Vivo Function of the Posterior Cruciate Ligament During Weightbearing Knee Flexion", The American Journal of Sports Medicine, Dec. 2004, pp. 1923-1928, vol. 32, No. 8, Publisher: American Orthopaedic Society for Sports Medicine, Published by SAGE; http://ajs.sagepub.com/content/32/8/1923.

Cascade, "Jack PCL Brace", Oct. 2004, Publisher: Cascade Orthopedic Supply, Inc., Published in: US. http://www.cascade-usa.com/customer/caorsu/images/PDF/SSN_jackPCL.pdf downloaded, 1 page.

Markolf, Keith L., et al., "Changes in Knee Laxity and Ligament Force After Sectioning the Posteromedial Bundle of the Posterior Cruciate Ligament", Arthroscopy: The Journal of Arthroscopic and Related Surgery, Oct. 2006, pp. 1100-1106, vol. 22, No. 10, Publisher: Arthroscopy Association of North America, Published in: US.

Papannagari, Ramprasand, et al., "Function of Posterior Cruciate Ligament Bundles During In Vivo Knee Flexion", The American Journal of Sports Medicine, Sep. 2007, pp. 1507-1512, vol. 35, No. 9, Publisher: American Orthopaedic Society for Sports Medicine, Published by SAGE; http://ajs.sage.pub.com/content/35/9/1507.

Bledsoe Axiom/Axiom-D Custom & Ots Knee Brace, "Application Instructions & Patient Manual: Instructions for ACL or PCL Symptoms", Jan. 2007, pp. 1-4, vol. CP020223, Rev B, Publisher: Bledsoe Brace Systems, Published in: US. http://www.bledsoebrace.com/pdf/AI/Axiom-AI.pdf.

Brochure: Armor Fourcepoint, Donjoy Product pages http://www.donjoy.com/armorfp. Downloaded, Oct. 2011, 2 pages. Published: US.

Brochure: "Fusion OA", Breg 360 Customer Care, Product page http://www.breg.com/knee-bracing/oa/fusion-oa.html, downloaded, Oct. 2011, 2 pages. Publisher: Orthofix, Published in: US.

Brochure: "Fusion XT OA", Bregg 360 Customer Care, Product page http://www.breg.com/knee-bracing/oa/fusion-xt-oa.html, downloaded, Oct. 2011, 2 pages. Publisher: Orthofix, Published in: US.

(56) References Cited

OTHER PUBLICATIONS

Brochure: "CTI Custom", OSSUR Product page from http://www.ossur.com/?PageID=13230 downloaded, Oct. 2011, 2 pages. Publisher: Ossur Americas, Published in: US.

Brochure: "X2K-OA", Bregg 360 Customer Care, Product page http://www.breg.com/knee-bracing/oa/x2k-oa.html. Downloaded, Oct. 2011, 1 page. Publisher: Orthofix, Published in: US.

Menetrey, Jacques, "PCL: Conservative Treatment", 4th Advanced Course on Knee Surgery, Jan. 22-27, 2012. http://www.kneecourse.com/download/seminar_2012/monday/MENETREY%20Conservative%20treatment.pdf, 37 pages.

Smith, Sean D. et al., "Functional bracing of ACL injuries: current state and future directions", Knee Surgery Sports Traumatology Arthhroscopy, Springer, Apr. 27, 2013, 11 pages.

Jansson, Kyle S. et al., "A Historical Perspective of PCL Bracing", Knee Surgery Sports Traumatology Arthhroscopy, Springer-Verlag, May 24, 2012, 7 pages.

Knapik, Joseph J. et al., Isometric, Isotonic and Isokinetic Torque Variations in Four Muscle Groups Through a Range of Joint Motion, "Physical Therapy: Journal of the American Physical Therapy Association and de Fysiotherapeut", vol. 63, No. 6, pp. 938-947, downloaded from http://ptjournal.apta.org/ on Apr. 15, 2014.

\* cited by examiner

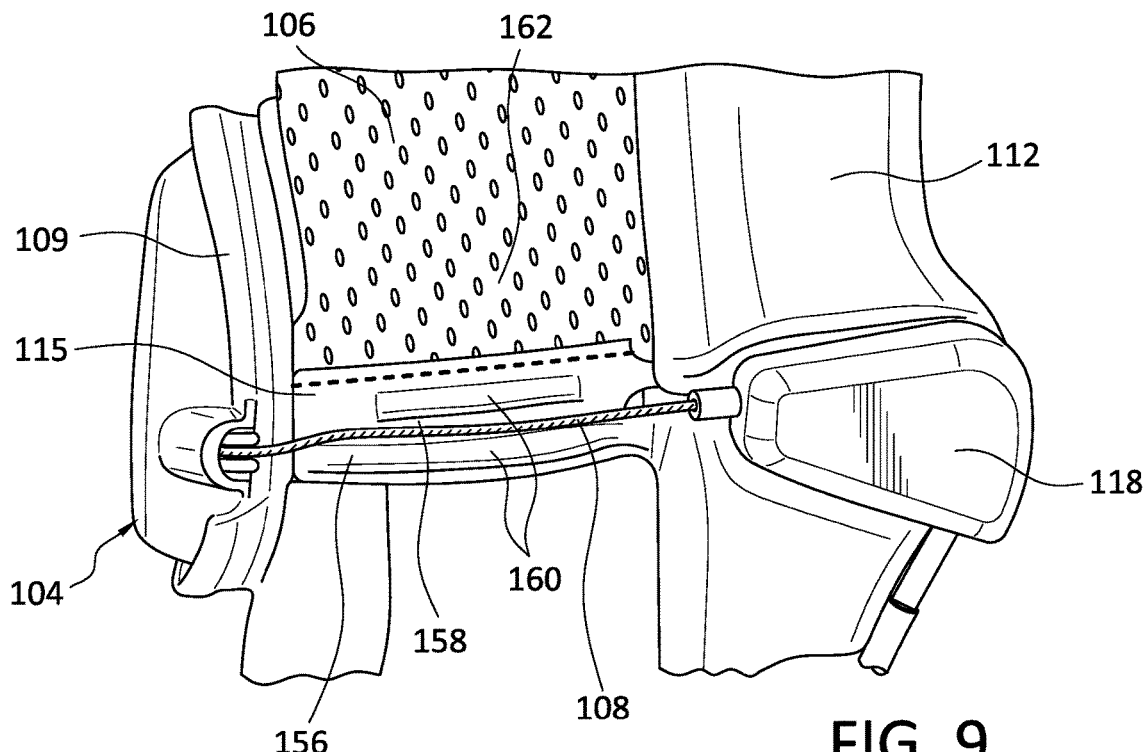
FIG. 9
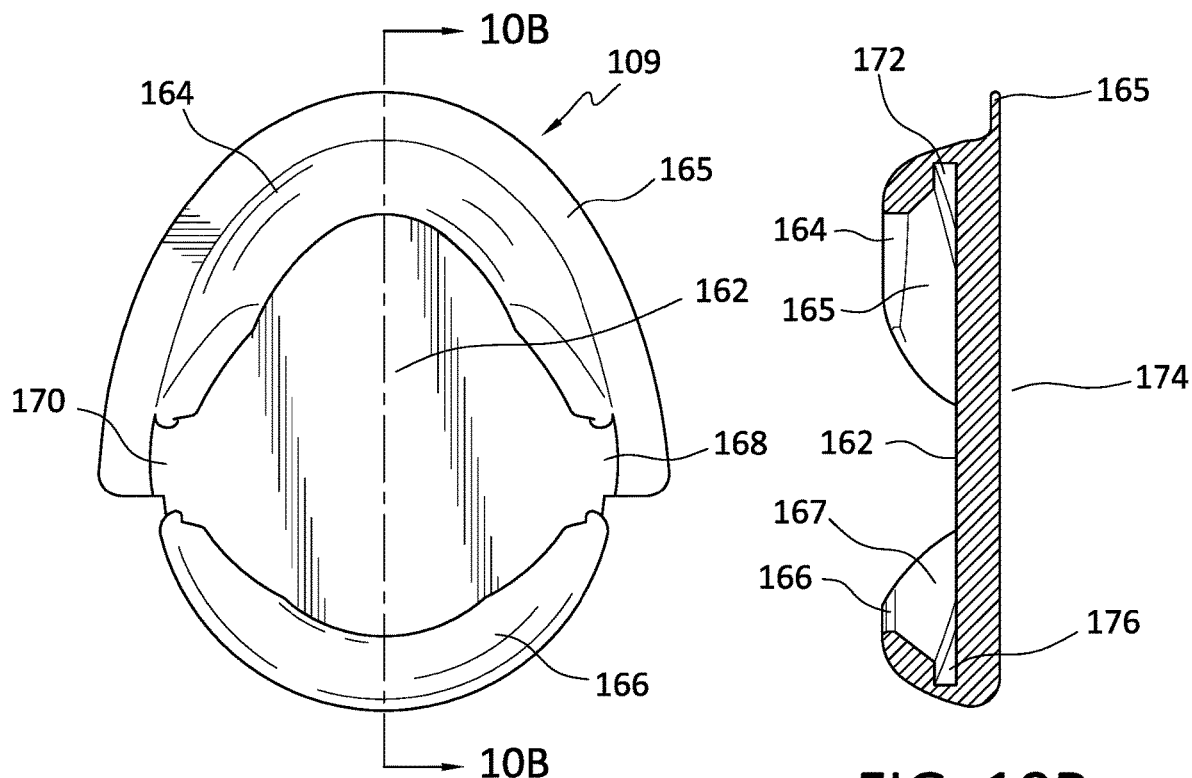
FIG. 10A
FIG. 10B

ORTHOPEDIC DEVICE HAVING A SUSPENSION ELEMENT

CROSS-REFERENCE TO RELATED APPLICATIONS

This application incorporates by reference in entirety the following: U.S. application Ser. No. 15/016,794, filed Feb. 5, 2016; U.S. application Ser. No. 14/926,098, filed Oct. 29, 2015; U.S. application Ser. No. 14/311,548, filed Jun. 23, 2014; U.S. application Ser. No. 14/334,152, filed Jul. 17, 2014; U.S. application Ser. No. 14/165,478, filed on Jan. 27, 2014; U.S. provisional application No. 61/756,754, filed on Jan. 25, 2013; U.S. provisional application No. 62/590,944, filed on Nov. 27, 2017.

FIELD OF THE DISCLOSURE

The disclosure relates to orthopedic devices, and more particularly to a suspension element and corresponding system for supporting a brace component.

BACKGROUND

Suspension systems are known in the art of orthopedic devices for supporting a mechanism, shell, strap or other component on the user's body. Known suspension systems have symmetric properties, such that they are elastic or inelastic uniformly in different directions, such as vertical and horizontal. As muscle tissue does not expand or contract uniformly or symmetrically, either during rest or movement, these suspension systems offer imperfect solutions for suspending brace components on the human body. Limbs are not of uniform dimensions and may form a variety of asymmetrical shapes.

The human thigh comprises quadriceps muscles, including the rectus femoris, vastus lateralis, vastus medialis, and vastus intermedius, that flex in different directions as the leg is moved, creating an asymmetric profile in flexion as compared to extension. Similar asymmetries are also observed in the lower leg, arms, shoulders, and other body parts. Components of an orthopedic device arranged statically over the thigh may apply pressure, padding, or other features to the leg asymmetrically during use, leading to sub-optimal bracing. A brace component may rather need to maintain its location at particular height of a body part but may need the ability to translate laterally along the height as the profile of the body part changes for best functionality.

Known suspension systems, such as straps or pads, seek to provide sufficient strength but consequently offer poor breathability. It follows that, to the contrary, if the suspension system is too breathable, it may not have sufficient strength to support the brace components. Often, to balance strength and breathability, suspension systems are bulky, uncomfortable, costly, and may limit mobility for users wearing the orthopedic device.

Suspension systems typically function only to support a brace component, and overlie on the user's body, serving as a buffer and carrier between the brace component and the user. The suspension systems do not interact or functionally operate with the brace component, adding to bulk and additional components, while missing an opportunity to offer better support of the brace component on the body.

Certain existing suspension systems have limited adaptability and freedom to cooperate with the user, being too rigid or too limited in degrees of freedom. Certain suspension systems are bound to the frame of an orthopedic device and are limited in motion and adjustability by the position of the frame.

Therefore there is a need for a suspension system that can better adapt to muscle tissue movement and the shape of a limb when worn with an orthopedic device. The suspension system must balance strength and breathability, and offer the ability to functionally operate with the brace component, the frame of the orthopedic device, or other brace components.

SUMMARY

According to an embodiment of the orthopedic device having a suspension element, the suspension element has properties permitting better control of a location of a brace component on a user's body, and enhanced tailoring of properties of the suspension element according to movement of the user. The suspension element therefore permits articulation of the brace component relative to the frame and can circumferentially secure to a user's anatomy without interference from the frame of the orthopedic device.

The suspension element may control the vertical position of a brace component, so the location of force exerted by the brace component is on a thigh and corresponding to a femur at a set height and centered on the leg of the user despite asymmetrical movements and/or shapes generated by the leg by having anisotropic properties. The suspension element is inelastic in the generally vertical position thereby controlling the height of the brace component to a desired location but is elastic in a generally horizontal position to stretch in left and right directions to accommodate differently sized legs and movement of the leg. In an alternative embodiment, the suspension element is elastic in the generally vertical position and is inelastic in the generally horizontal position.

In another embodiment, the suspension element may control the position of a brace component with an advantageous shape of the suspension element and/or connecting portions between the orthopedic device and the suspension element, allowing the suspension element and brace components suspended therefrom to articulate independently and/or relative to the frame of the orthopedic device. A suspension element may comprise a geometry, such as a tapered portion, hourglass shaped portion or suitable shape, at which the suspension element attaches to the frame, additionally with straps forming a circumferential loop around the user's anatomy and independent of the frame. The circumferential loop adapts and conforms to an individual, asymmetric shape of a user's leg without interference from the frame of the orthopedic device.

An exemplary brace component is a tensioning mechanism capable of tensioning a cable or cable segments relative to a frame of the orthopedic device, although other brace components may be used when suspension of such brace component is desired.

The suspension element is lightweight, low-profile, and significantly breathable when compared to conventional textile or polymeric straps. The suspension element covers significant surface area to better distribute pressure over a user's leg, as opposed to a strap or pad located in a limited, discrete area and applying pressure only in such area. The larger coverage of surface area may improve proprioception of the orthopedic device and encourage users to more consistently wear the orthopedic device, thus enhancing the effectiveness of the orthopedic device and resulting in safer use of the orthopedic device. The larger surface area coverage navigates the tension between breathability and strength, as breathability features may be provided in sufficient quantities for enhanced breathability and distributed over enough area to not compromise overall strength of the suspension element.

The suspension element is arranged to move or articulate relative to the frame of the orthopedic device in a controlled manner. In the instance of the suspension element having anisotropic properties, the controlled manner relates to movement or articulation in desired directions and to desired degrees, while comparatively restricting movement in other directions, due to anisotropic properties of the suspension element and/or due to the shape and arrangement of components. In the instance of the suspension element having geometrical properties, the controlled manner of the suspension element is arranged to allow the brace component to move or pivot relative to the frame only in desired directions and to desired degrees. It will be noted that the suspension element may be configured in combination with the features of both anisotropic properties and geometry to achieve the articulation in a controlled manner.

The suspension element is adapted to cooperate with the brace frame or features depending therefrom, and the brace component to better interlock such features of the orthopedic device. The suspension element is provided with features to increase durability, particularly in combination with features of a brace component such as cables extending therefrom and cooperating therewith.

The suspension element is arranged to securely and efficiently connect to the frame of the orthopedic device. The suspension element may be cheaper to provide in comparison to foam or textile materials used in conventional orthopedic devices, owing to its simplified construction.

The numerous other advantages, features and functions of embodiments of an orthopedic device having a suspension element will become clear and better understood in view of the following description and accompanying drawings.

BRIEF DESCRIPTION OF THE DRAWINGS

The drawing figures are not necessarily drawn to scale, but instead are drawn to provide a better understanding of the components thereof, and are not intended to be limiting in scope, but to provide exemplary illustrations. The figures illustrate exemplary configurations of an orthopedic device having a suspension element, and in no way limit the structures or configurations of an orthopedic device having a suspension element according to the present disclosure.

FIG. 9 is a schematic view showing a reinforced edging of the suspension element in FIG. 2A.

FIG. 10A is a front elevational view of a retainer for a tensioning mechanism.

FIG. 10B is a cross-sectional view taken along line 10B-10B in FIG. 10A.

DETAILED DESCRIPTION OF VARIOUS EMBODIMENTS

Figure 1:
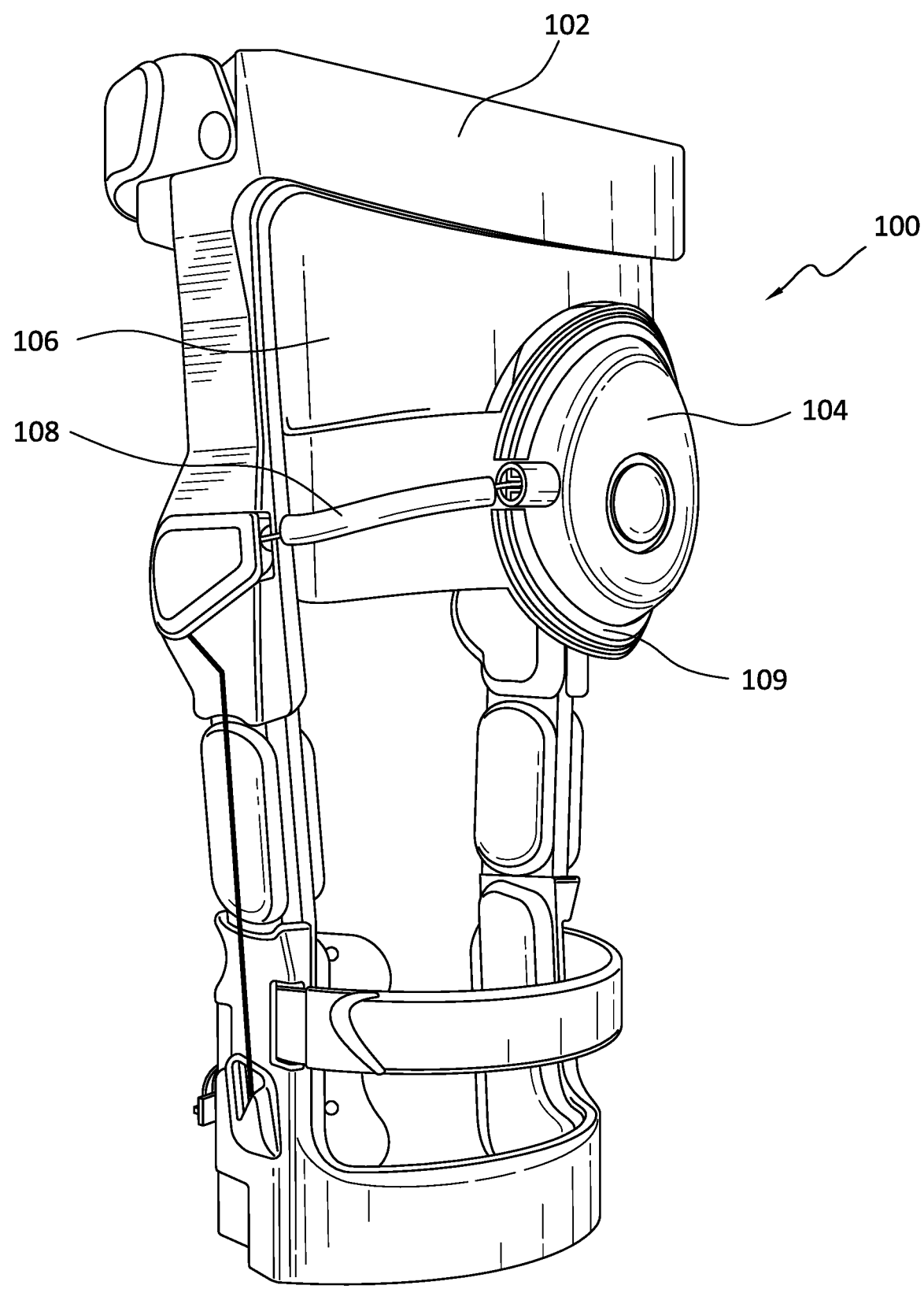
FIG. 1 is a perspective view of an orthopedic device having a suspension element.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the invention covers all modifications, alternative constructions, combinations, and equivalents falling within the spirit and scope of the disclosure.

It will be understood that, unless a term is defined to possess a described meaning, there is no intent to limit the meaning of such term, either expressly or indirectly, beyond its plain or ordinary meaning.

For ease of understanding the disclosed embodiments of an orthopedic device having a suspension element, the anterior and posterior portions of the orthopedic device may be described independently. Anterior and posterior portions of the orthopedic device function together to support and stabilize anatomical portions of the user of the device.

For further ease of understanding the embodiments of an orthopedic device as disclosed, a description of a few terms, when used, is necessary. As used, the term "proximal" has its ordinary meaning and refers to a location next to or near the point of attachment or origin or a central point, or located toward the center of the body. Likewise, the term "distal" has its ordinary meaning and refers to a location situated away from the point of attachment or origin or a central point, or located away from the center of the body. The term "posterior" also has its ordinary meaning and refers to a location behind or to the rear of another location. Lastly, the term "anterior" has its ordinary meaning and refers to a location ahead of or to the front of another location.

The terms "rigid" and "flexible" may distinguish characteristics of portions of certain features of the orthopedic device. The term "rigid" should denote an element of the device is generally devoid of flexibility. Within the context of frame or support members or shells that are "rigid," it should indicate that they do not lose their overall shape when force is applied, and they may break if bent with sufficient force. As for the term "semi-rigid," this term is used to connote properties of features that provide support and are free-standing; however such features may have some degree of flexibility or resiliency. The term "flexible" should denote that features are capable of repeated bending such that the features may be bent into retained shapes or the features do not retain a general shape, but continuously deform when force is applied. The term "resilient" is used to qualify such flexible features as generally returning to an initial general shape without permanent deformation.

The orthopedic device described in this disclosure resembles a variation of the orthopedic device described and shown in U.S. application Ser. No. 15/016,794, and is incorporated and modified according to this disclosure. Using the features, components, properties and uses described herein, however, are not limited to being used in the orthopedic device of U.S. application Ser. No. 15/016, 794, but may be considered useful in other orthopedic or medical devices.

FIG. 1 depicts in perspective view an orthopedic device 100 having a suspension element 106. The orthopedic device 100 may comprise a frame 102 having upper and lower parts corresponding to a user's upper and lower legs, respectively. The suspension element 106 suspends a brace component 104 over a portion of the user's leg, with the brace component 104 having a cable or cable segments 108 attaching to the frame 102. Straps, hinges, and other orthopedic components may be provided along the frame 102. In the depicted embodiment, the brace component 104 is suspended independently and circumferentially by the suspension element 106 over and about the user's thigh.

Figure 2A:
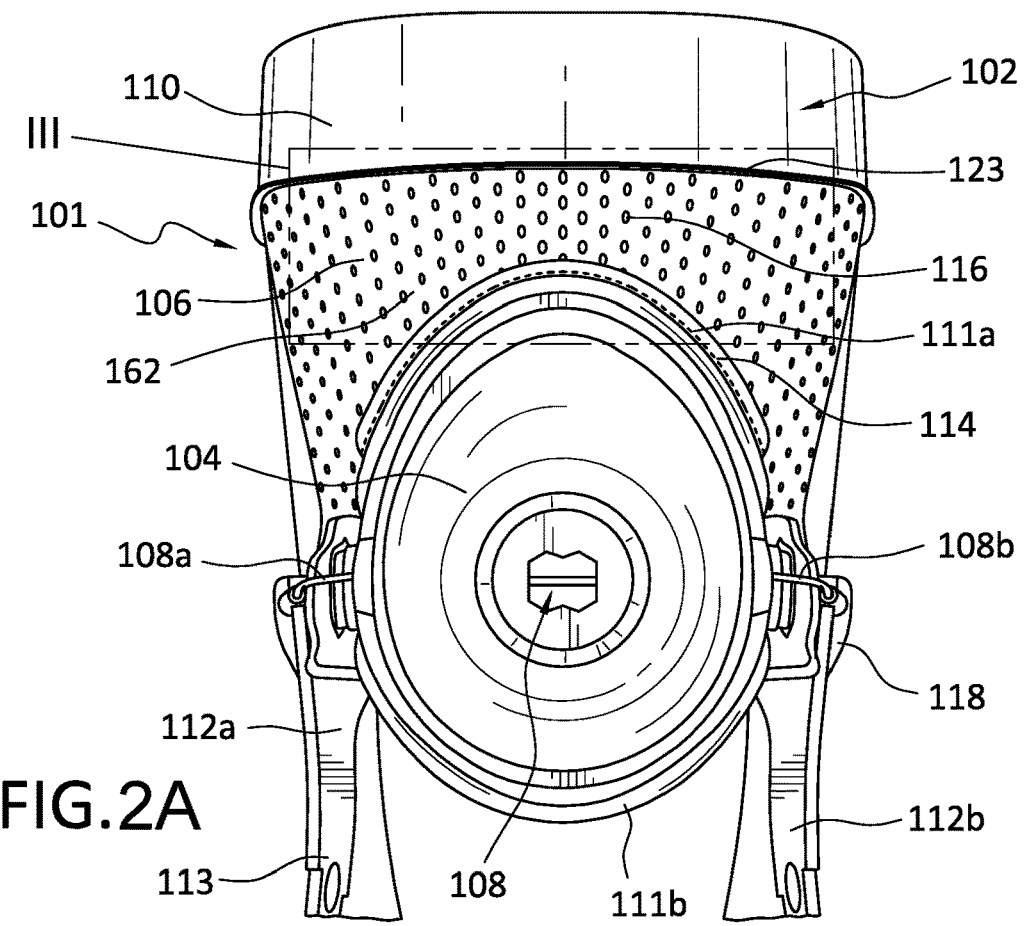
FIG. 2A is a front view of an embodiment of the orthopedic device having a suspension element of FIG. 1.

FIG. 2A illustrates a front elevational view of the orthopedic device 100 having the frame 102, the brace component 104, and the suspension element 106 supporting the brace component 104, and connecting the brace component 104 to the frame 102 such that the suspension element 106 has anisotropic properties. The anisotropic properties include the suspension element 106 being generally or completely inelastic in a vertical direction and generally elastic in a horizontal direction. In other embodiments, the suspension element 106 is inelastic in a horizontal direction and elastic in a vertical direction.

In an exemplary embodiment, the suspension element 106 is a flexible mesh sheet having the aforementioned anisotropic properties. The mesh sheet may define a plurality of openings 116 arranged in a predetermined pattern, as shown in the illustrated embodiments. The openings 116 may have a shape or configuration that permits elasticity in a particular direction and inelasticity in another direction, and/or may be arranged in a pattern that provides anisotropic properties. The openings 116 may be further arranged for enhanced breathability. In other exemplary embodiments, the suspension element 106 may be a polymeric sheet exhibiting the desired anisotropic properties and may be breathable by having porosity. Other materials may be used for the suspension element, particularly those with anisotropic properties. The suspension element 106 may be arranged as a flexible sheet. As regards "flexible," the suspension element 106 may be easily pliable and bendable from a first configuration to a second configuration without readily compromising the integrity of the suspension element 106.

In the illustrated embodiment, the anisotropic properties of the suspension element 106 permit better and independent control of a location of a brace component 104 on a user's body, and the inelastic/elastic properties of the suspension element 106 may be tailored to the anatomy and movement of the user. The suspension element 106 may control the vertical position of a brace component 104 so the location of force exerted by the brace component 104 is on a user's femur at a set height and centered on the leg of the user. The suspension element 106 is inelastic in the generally vertical direction, thereby controlling the height of the brace component 104, but is elastic in a generally horizontal position to stretch in left and right directions, accommodating differently sized legs and certain asymmetrical muscle/leg movements without causing undesired translations of the brace component 104 or the orthopedic device 100, and without causing discomfort such as through pressure points.

As regards "anisotropic," the suspension element 106 may have different properties in different directions. The suspension element 106 may be more elastic in certain directions than in other directions, or may be elastic in a certain direction and devoid of elasticity or inelastic in another direction. The different properties may stem from different materials, different shapes, both, or other factors.

The suspension element 106 is lightweight, low-profile, and significantly breathable when compared to conventional textile or polymeric straps. The suspension element 106 covers significant surface area to better distribute pressure over a user's leg, as opposed to a strap or pad located in a discrete area and applying pressure only in such area, which can lead to pressure points, discomfort, improper use, and undesired translation of the brace component 104 along a user's leg. The larger coverage of surface area by the suspension element 104 may improve proprioception of the orthopedic device 100, and thereby encourage users to more consistently wear the orthopedic device 100.

The suspension element 106 is adapted to cooperate with the frame 102 or features depending therefrom, and the brace component 104, to better interlock such features of the orthopedic device 100. The suspension element 106 is provided with features to increase durability, particularly in combination with features of the brace component 104 such as cables extending therefrom.

The suspension element 106 is arranged to securely and efficiently connect to the frame 102 of the orthopedic device 100. The suspension element 106 may be significantly cheaper to provide in comparison to foam or textile materials used in conventional orthopedic devices, owing to its simplified construction. In the depicted embodiment, there are no straps, buckles, tensioners, or other components associated with the suspension element 106, facilitating a suspension element that is easier and cheaper to produce with its attendant functional advantages.

The exemplary brace component 104 is described as a tensioning device that is similar to the tensioning mechanism described in U.S. application Ser. No. 14/311,548. The teachings of the disclosure pertaining to the exemplary brace component 104, including providing improved breathability, strength, and anisotropic properties through the suspension element 106, may be applied to any component of any brace device. Other brace components may include stays, struts, padding, straps, and other common components found in the bracing arts.

In the illustrated embodiment, the brace component 104 is a tensioning device 104 which includes at least one cable 108 extending to the frame 102. A body 105 of the tensioning device 104 is substantially rigid, particularly compared to the suspension element 106 which is flexible, particularly relative to the frame 102. A guide 118 is secured to the frame 102 and receives the at least one cable 108, to be routed along the frame 102 as indicated in known braces. The guide 118 advantageously secures the at least one cable 108 to the frame but shrouds the cable 118 at the sides of the frame 102 such that interference with or damage to the at least one cable 118 by outside contact is avoided.

The frame 102 includes a first portion 110 extending between first and seconds struts 112a, 112b the first and second struts 112a, 112b arranged on medial and lateral sides of the orthopedic device 100. The tensioning device 104 includes a peripheral edge 114 securing to the suspension element 106. The frame 102 is rigid and the suspension element 106 is flexible, particularly compared to both the frame 102 and the tensioning device 104.

Figure 2B:
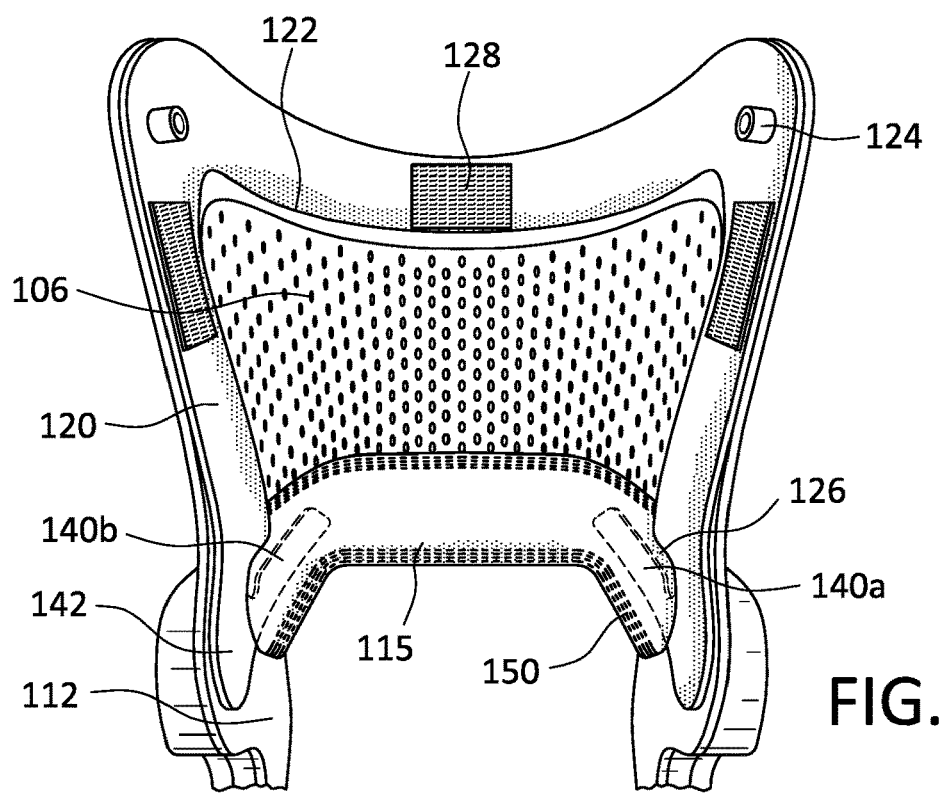
FIG. 2B is a rear view of the embodiment of FIG. 2A.

As shown in the exemplary embodiment of FIGS. 2A and 2B, the suspension element 106 is enclosed by the frame 102 and the tensioning element 104. A periphery of the suspension element 106 is connected to both the frame 102 and the tensioning element 104. An entirety of a periphery of the suspension element 106 may be enclosed by the frame 102 and the tensioning device 104, inclusive of arms of the tensioning device described below, such that the suspension element 106 spans a space between the tensioning device 104 and the frame 102. However, a reinforcement edging either applied onto or forming part of the suspension element 106 may likewise form part of the periphery of a mesh sheet of suspension element 106 entirely enclosed by the frame 102 and the tensioning device 104.

The tensioning device 104 suspends from the suspension element 106, whereby with the illustrated embodiment, the tensioning device 104 hangs from a lower or distal portion of the suspension element 106, and the sides of the tensioning device 104 connect medially and laterally to first and second struts 112a, 112b. The first and second struts 112a, 112b may extend distally beyond the tensioning device 104 in a direction away from the first portion 110 of the frame 102 such that the tensioning device 104 is between the first portion 110 and end portions 113 of the first and second struts 112a, 112b. This arrangement permits the tensioning device 104 to be adjustable relative to the first portion 110 and the first and second struts 112a, 112b to accommodate a user's anatomy.

The tensioning device 104 may be arranged to translate laterally to be closer to the first strut 112a during a flexion motion of the leg, and centrally between the first and second struts 112a, 112b during extension. The tensioning device 104 may remain at a same height during his lateral/medial translation owing to the anisotropic properties of the suspension element 106, preventing elongation and displacement in vertical directions.

Figure 3:
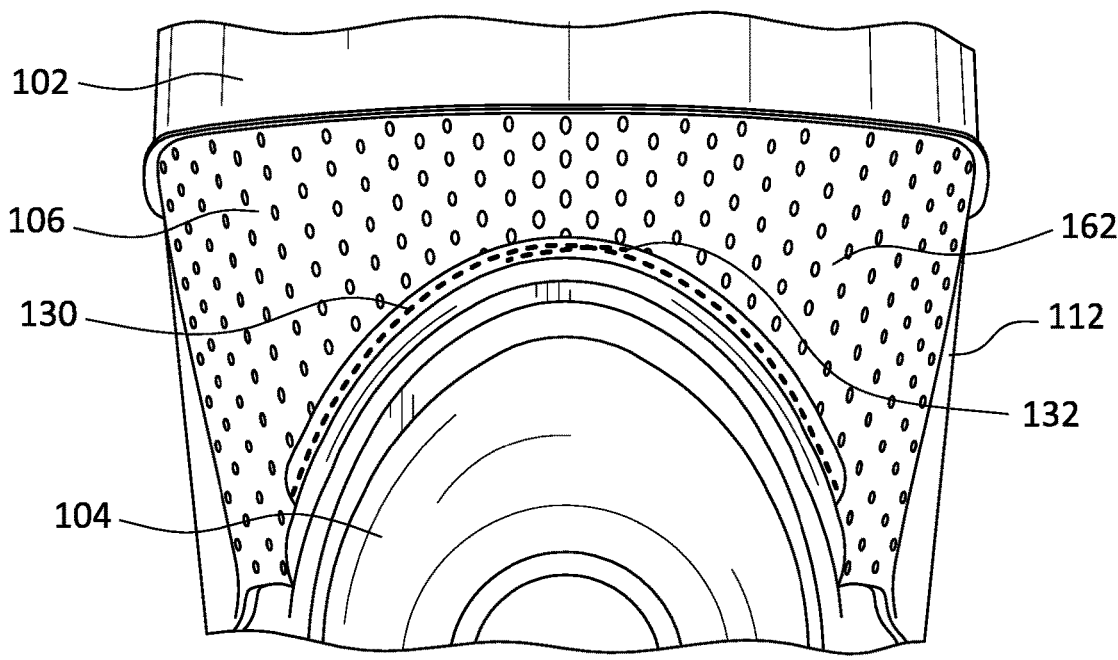
FIG. 3 is a detail view taken from detail III in FIG. 2A.

According to FIG. 3, the suspension element 106 only secures along a first segment to the tensioning device 104, a second segment of the tensioning device 104 being devoid of the suspension element 106. A first segment 111a of the tensioning device 104 is directed proximally toward the first portion 110, whereas the second segment 111b of the tensioning device 104 is located opposite to the first segment 111a and extends distally toward the end portions 113. In an exemplary embodiment only the first segment 111a defines a flange or peripheral edge 114. The flange 114 is preferably flexible relative to the body 105 of the tensioning device 104. The suspension element 106 is shown as being stitched to the flange 114, but may be secured thereto with other means such as adhesive, co-molding, or fasteners (either permanent such as by rivets or removable such as by hook and loop), facilitating easy removal, cleaning, and/or replacement of the suspension element 106 and/or the tensioning device 104.

Figure 4:
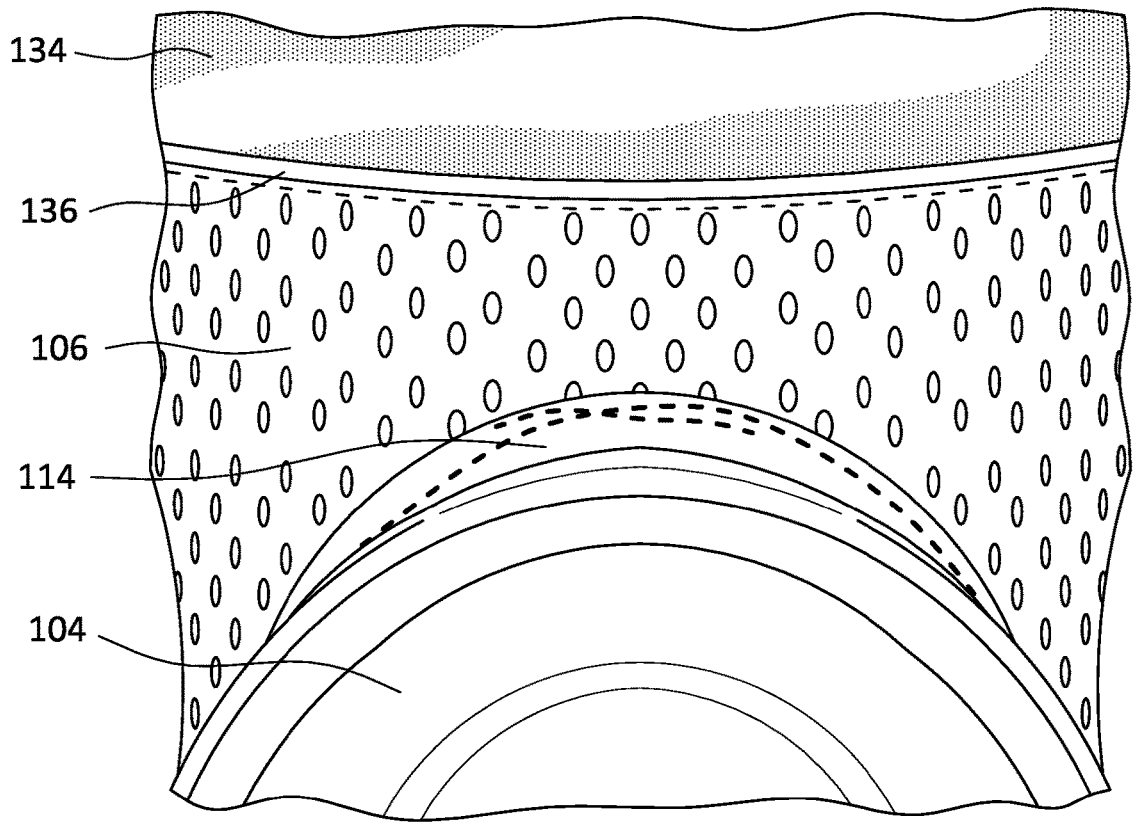
FIG. 4 is a detail view showing a different embodiment of a frame in the orthopedic device having an anisotropic suspension element.

FIG. 4 shows that the frame 102 may have a covering 134, such as a metal frame being encased by foam, whereby a segment of a periphery 136 of the suspension element 106 is secured to the covering 134. The covering 134 may be a polymeric material having compressibility greater than the frame 102, and the frame material surrounded by the covering 134 may be a rigid material. The rigid material may be a malleable metal, including aluminum, or other materials such as titanium, steel, composite, etc. Preferably, however, the covering 134 is softer than the material forming the frame 102. In other embodiments, the covering 134 may be formed from a polymeric overmold.

Referring to FIG. 2B, an interface 120 is secured along the frame 102, and the suspension element 106 secures along the interface 120. The interface 120 is preferably a flexible material arranged to generally conform to the shape of the frame 102, and is easier to adhere or secure the suspension element 106 to than the frame 102. In an exemplary embodiment, the interface 120 is a plastic material, and the frame 102 is substantially more rigid than the interface 120. The interface 120 is attached to the frame 102 by at least one fastener 124, or by other known means. The interface 120 may further offer comfort and pressure relief to a user, as the interface 120 may be disposed on an inner surface of the frame 102.

The interface 120 defines an inner peripheral edge 122 along which the suspension element 106 secures. The peripheral edge 122 may be coextensive with an inner peripheral edge 123 of the frame 102, and a peripheral edge of the suspension element 106 may be located or secured between the peripheral edges 122, 123 of the frame 102 and the interface 120, respectively. As shown, the peripheral edge of the suspension element 106 is stitched or fastened along the peripheral edge 122 of the interface 120. The interface 120 alternatively or additionally may include a plurality of fastener elements 128 for engaging padding and/or a liner for securing along the frame 102. The fastener elements 128 may comprise hook and loop fastener or any other suitable fastening device.

Figure 7:
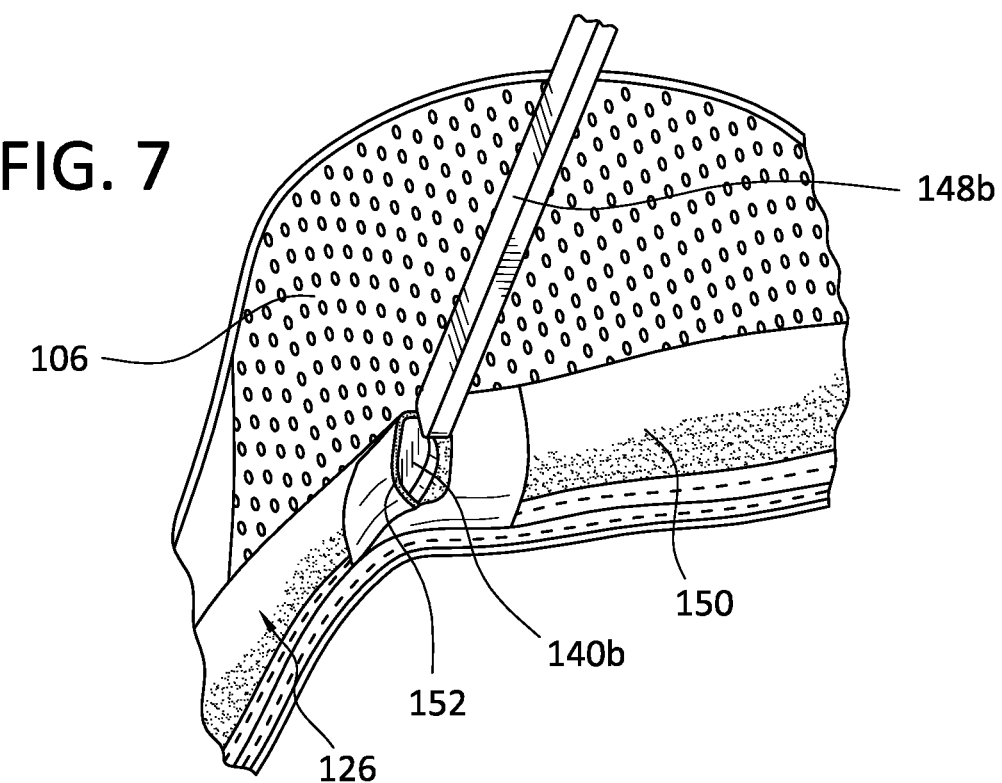
FIG. 7 is a schematic view of overlaying an arm of a tensioning mechanism over an arm of a support interface in the orthopedic device of FIG. 2A.
Figure 8:
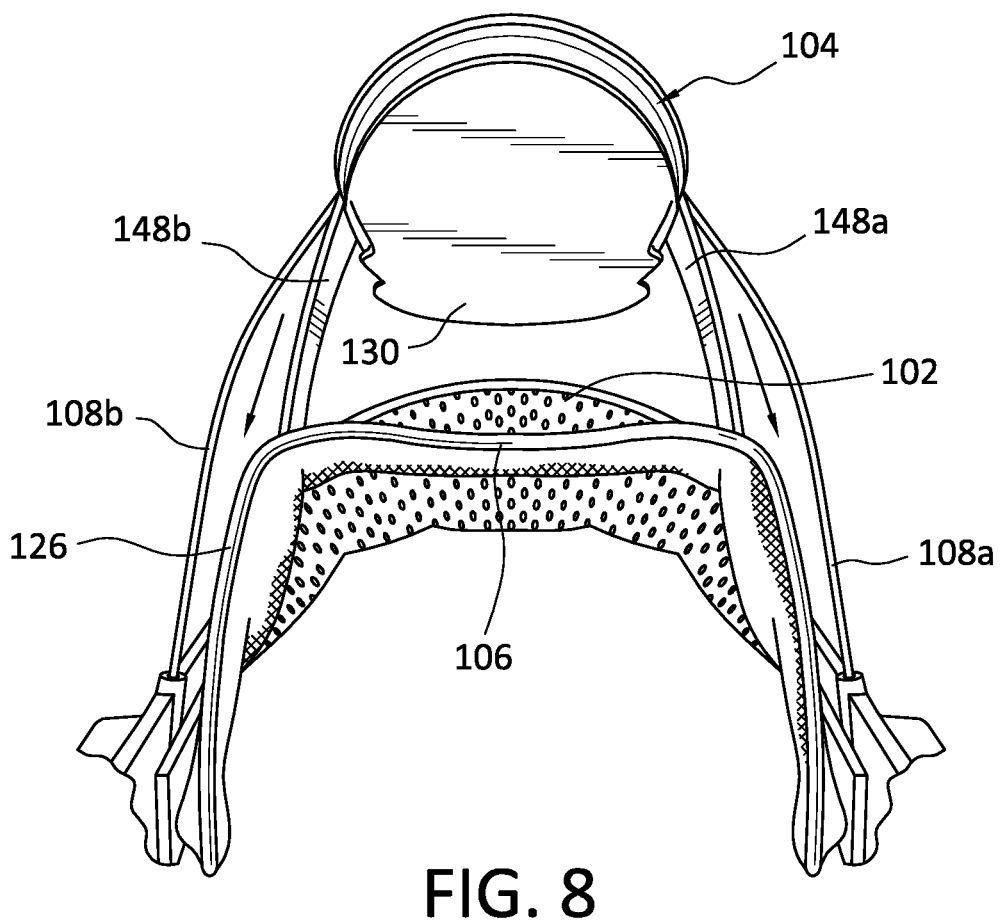
FIG. 8 is a schematic view showing flexibility of arms of a tensioning mechanism being inserted into sleeves of the suspension element.

Turning to FIGS. 2B, 7, and 8, an embodiment of the orthopedic device is depicted, wherein the suspension element 106 defines a sleeve portion 126 located along a periphery thereof, for example along a side not arranged along the frame 102. The sleeve portion 126 is preferably formed from a more resilient, stiffer, and/or rigid material than a material forming a sheet portion 162 of the suspension element 106 outside of the sleeve portion 126.

The sleeve portion 126 may include a padded section 115 located along an inner side of the sleeve portion 126. The padded section 115 extends underneath and underlies the tensioning device 104 and the cables 108 or other elements extending therefrom along at least a portion thereof to provide greater comfort to a user and to eliminate or mitigate pressure points by extending between the user's skin and any rigid components of the orthopedic device 100.

Figure 5:
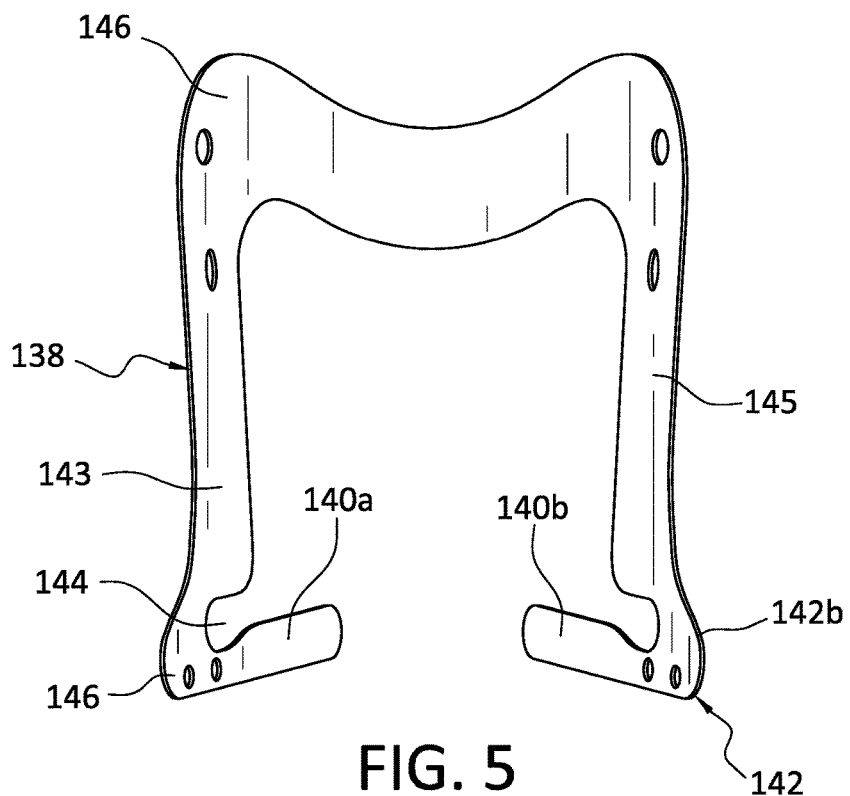
FIG. 5 is a schematic view of a support interface for connecting a suspension element to a frame of an orthopedic device.

Turning now to FIG. 5, a support interface 138 for securing a suspension element to an orthopedic device defines a first portion 146 spanning a distance between first and second segments 143, 145, the first portion 146 generally corresponding in profile/shape to the first portion 110 of the frame 102, and the first and second segments 143, 145 generally corresponding to the first and second struts 112a, 112b of the frame 102. The interface 138 defines first and second wings 140a, 140b extending from corner portions 142 of the first and second segments 143, 145, the first and second wings 140a, 140b extending into the sleeve portion 126 of the suspension element 106. The interface 138 defines first and second corner portions 142a, 142b and a joint 144 at the corner portions 142a, 142b between the first and second segments 143, 145, the joint 144 defining a recessed opening between the first and second segments 143, 145 and the first and second wings 140a, 140b. The first and second wings 140a, 140b flexibly depend from the corner portions 142a, 142b. By providing portions 146, segments 143, 145, and wings 140a, 140b, the support interface 138 may closely track the shape of a frame 102 and provide a secure attachment of a suspension element between the support interface 138 and the frame 102.

Figure 6:
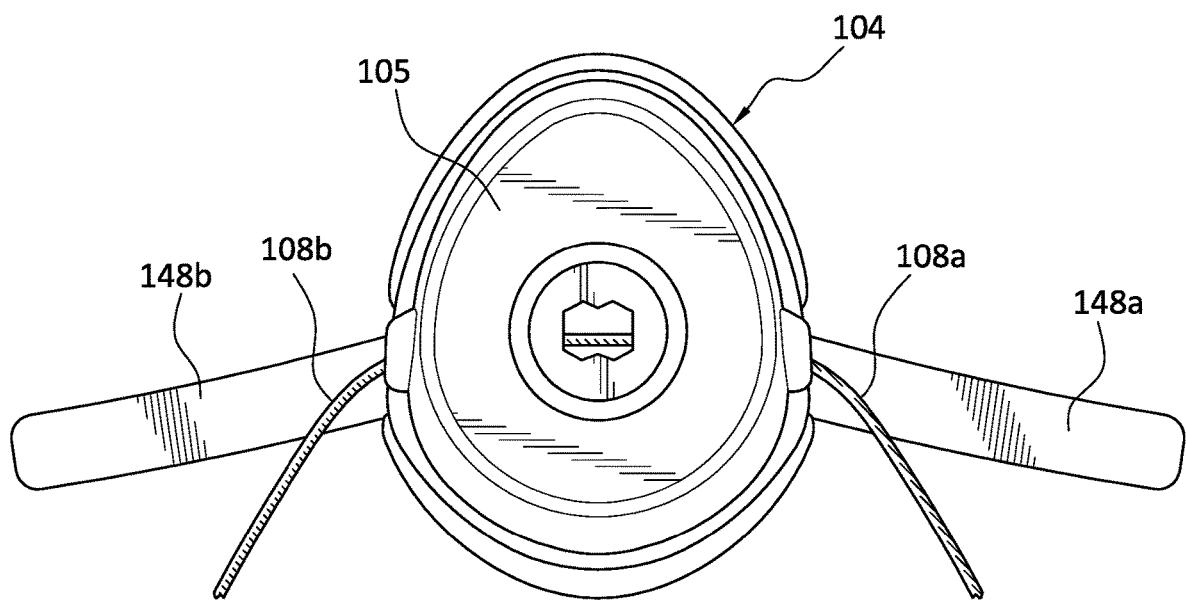
FIG. 6 is a detail view of a rear side of a tensioning mechanism in the orthopedic device of FIG. 2A.

Turning now to FIGS. 6, 7, and 8, the tensioning device 104 defines first and second arms 148a, 148b arranged to extend into the sleeve portion 126, and to overlap at least in part with the first and second wings 140a, 140b of the support interface 138 in the sleeve portion 126. First and second portions of the cables 108a, 108b likewise extend from the tensioning device medially and laterally, respectively. The sleeve portion 126 defines an opening 152 into which the first and second arms 148a, 148b extend. The sleeve portion 126 is formed at least in part by a reinforced edge 150 of the suspension element 106, which may be formed by stitching, adhesives, added material, or other suitable means. The reinforced edge 150 may define a channel through which the first and second arms 148a, 148b may extend and translate.

The first and second wings 140a, 140b of the support interface 138 and the first and second arms 148a, 148b of the tensioning device 104 extend in opposed directions relative to one another in the sleeve portion 126, overlapping over at least a portion of each respective pair of wings and arms. The wings and arms may increase or decrease the degree of overlap as the tensioning device 104 translates medially or laterally relative to the frame 102.

In an embodiment, the first and second arms 148a, 148b may define an inner channel or cavity sized and configured to allow a respective one of the first and second wings 140a, 140b to enter and translate within. As the tensioning device 104 moves laterally or medially at a fixed height in response to a changing configuration of the user's leg, the wings 140a, 140b may extend into the cavity defined within the arms 148a, 148b to a different extent allowing the degree of overlap to be variable. In other embodiments, the arms 148a, 148b and wings 140a, 140b may overlap in different suitable manners.

By providing the first and second arms 148a, 148b and the first and second wings 140a, 140b with a variable degree of overlap, and in combination with the suspension element 106, the suspension element 106 may move relative to the frame 102 in a controlled manner. As regards to the term "controlled manner," the suspension element 106 facilitates movement in desired directions and to desired degrees, while comparatively restricting movement in other directions, due to anisotropic properties of the suspension element 106 and/or due to the shape and arrangement of components such as the arm and wing combinations within the sleeve portion 126.

The first and second arms 148a, 148b flexibly extend from the tensioning device 104. The cables 108a, 108b engage a winding mechanism (not shown) of the tensioning device 104 and at least a portion of the cables 108a, 108b extend over the first and second arms 148a, 148b as the cables 108a, 108b extend towards the frame 102. By providing the overlapping arrangement of the first and second wings 140a, 140b with the respective arms 148a, 148b of the tensioning device 104, the suspension element 106 can suspend the tensioning device 104 in a manner that ensures that the tensioning device 104 is suspended at a fixed height relative to the frame 102, but in a variable lateral location that may change based on the configuration of the user's leg.

The arrangement of the wings 140a, 140b and arms 148a, 148b to be partially overlapping on either side of the tensioning device 104 allows the tensioning device 104 to secure to the frame 102 without being limited in its needed movement by the frame 102, such as if the tensioning device 104 were secured via a strap to the frame 102. The tensioning device 104 is independently movable relative to the frame 102 as the degree of overlap between respective wings 140a, 140b and arms 148a, 148b changes during use, allowing for greater flexibility as the user's leg changes in dimensions and the tensioning device 104 is required to shift either laterally or medially to provide optimal functionality.

Turning now to FIG. 9, the reinforced edge 150 defines a covering 156 over which the cable ends 108a, 108b are arranged to extend. The covering 156 may be formed from a polymeric material that is formed over and interlocks with the sheet material of the suspension element 106. The covering 156 is formed from a material more resilient, thicker and/or tougher than the sheet portion 162. The covering 156 defines at least one bolster 160, preferably at least two, that forms a channel 158 along which the cable ends 108a, 108b extend. The channel 158 maintains the path of the cable 108 relative to the tensioning device 104, according to placement or suspension by the suspension element 106.

FIG. 8 shows the tensioning device 104 in a maximum translation location. The flange 130, when secured to the suspension element 106, will cause the suspension element 106 to stretch to allow the entire assembly (inclusive of the tensioning device 104 and the suspension element 106) to move to this position. As the cable 108 is tightened, the tensioning device 104 will move closer to the suspension element 106 and the arms 148a, 148b will move relative to the subshell extensions in the directions of the arrows.

FIGS. 10A and 10B depict a retainer such as a cradle 109 capable of removably holding the brace component 104 of the aforementioned embodiments. The cradle 109 may be formed from a resilient and semi-rigid material enabling the brace component 104 to be wedged among features of the cradle 109 and held in place during use. The cradle 109 may be formed from an EVA (i.e., ethylene-vinyl acetate) to better enable manipulation of the cradle 109 for adding and removing the brace component 104, and adapting to the anatomy of the user upon which the cradle 109 is placed.

The cradle 109 may be formed from a resilient and structural foam, such as a closed-cell foam as in EVA, to provide cushioning and comfort when or as the brace component 104 presses against or toward a user's anatomy, and allowing the structures defined by the cradle 109 to return to their original configuration after a force has been applied and released. For instance, a user or clinician may insert the brace component 104 into the cradle 109 by temporarily deforming resilient structures defined thereon and allowing the resilient structures to return to their original shape around the brace component 104, holding the brace component 104 in place.

The cradle 109 provides ease of use on initial fitting, and serves as a buffer between the brace component 104 and with a brace liner, as discussed in greater detail below. The cradle 109 preferably has at least one attachment segment 169 adapted to secure to the suspension element 106, such as by stitching or adhesive, and may be segmented about the periphery of the brace component 104. The cradle 109 is not limited to EVA or closed-cell foam; rather, any suitable material may construct the cradle 109, especially regarding the resilience and manipulability of the cradle 109 in the depicted embodiment.

The cradle 109 may have a securing feature such as at least two resilient lips 164, 166 adapted to secure about and over at least a portion of the brace component 104. In the depicted embodiment, the at least two lips 164, 166 are opposed to one another and spaced apart by clearances 168, 170 formed alongside portions of the cradle 109, whereas the at least two lips 164, 166 are located at upper and lower portions of the cradle 109, respectively. The cradle 109 may include more than two lips adapted to secure about the periphery of the brace component 104, however in the depicted embodiment, the clearances 168, 170 are provided as passageways for cable segments extending from side portions (i.e., lateral and medial sides) of the brace component 104.

The first lip 164 has an overhang or contoured flange 165 adapted to extend over an upper portion of the brace component 104. A first groove 172 is provided to fittingly correspond to a peripheral edge of the brace component 104. The second lip 166 likewise has an overhang or contoured flange 167 adapted to extend over a lower portion of the brace component 104. The second groove 176 is also provided to fittingly correspond to a peripheral edge of the brace component 104.

The cradle 109 has a front, inner surface 162 contoured for the brace component 104 to abut against. The cradle 109 also has a rear outer surface 174 that may be contoured or define a contoured profile according to corresponding anatomy or anatomical profiles or geometry against which the cradle 109 is placed; for example, the contoured profile defined by the outer surface 174 may define a concavity arranged to closely and fittingly engage with the user's thigh.

Contours of the inner and outer surfaces 162, 174 may share the same shape, or alternatively there may be a mismatch if the surface of the brace component 104 differs from the anatomical surface upon which the inner and outer surfaces abut, respectively. As shown in following embodiments, a padding or liner may be located between the cradle 109 and the anatomy. The means for retaining the brace component 104 by the cradle 109 is exemplary and may be adapted to the shape of the brace component 104.

Figure 11:
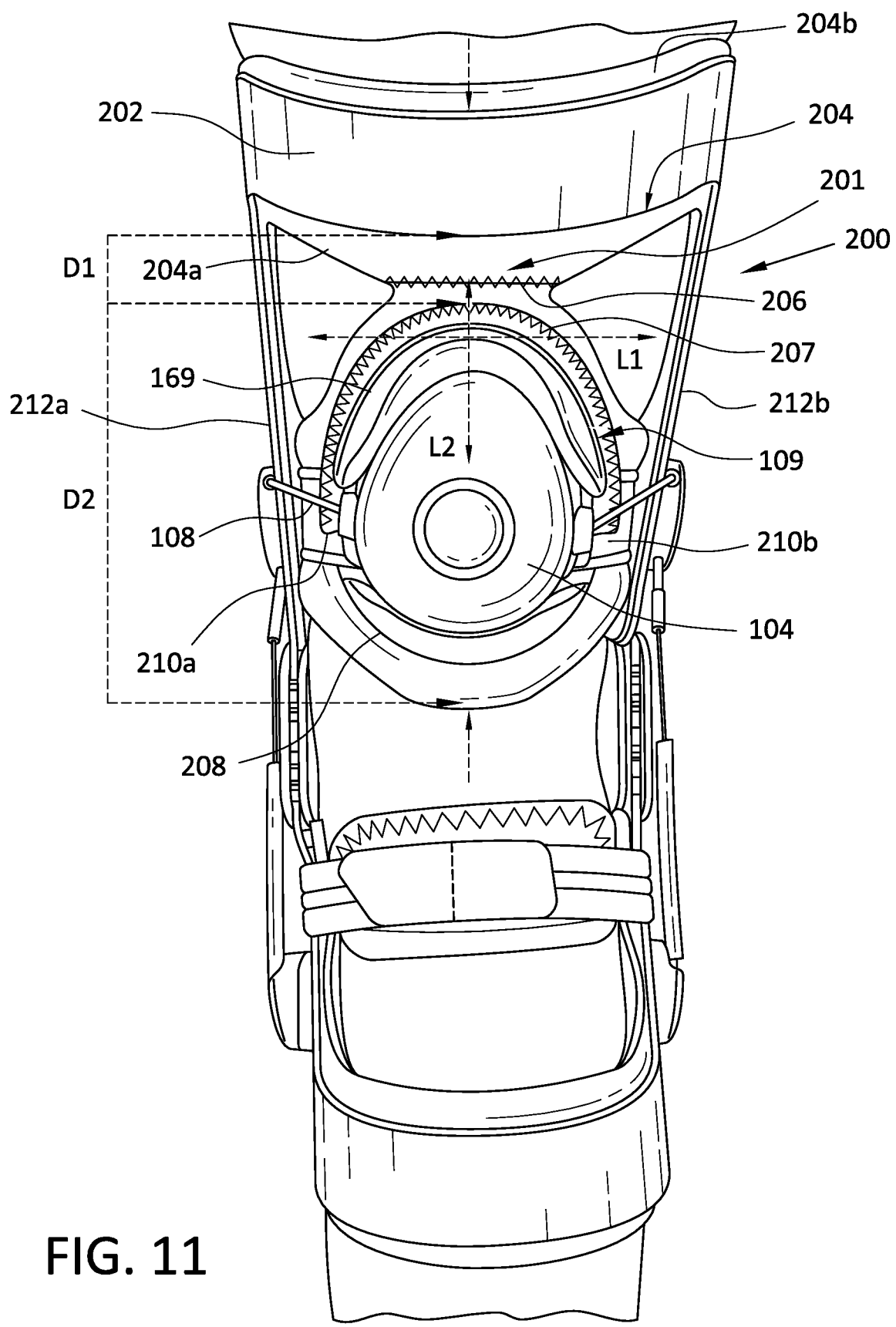
FIG. 11 is an elevational view showing another orthopedic device having another embodiment of a suspension element.

FIG. 11 exemplifies another embodiment of an orthopedic device 200 with a suspension element 201 arranged to position a brace component 104, as discussed in the foregoing embodiments. The orthopedic device 200 may be similar to the orthopedic device 200 of FIG. 1, and has a frame 202 which may be rigid. A frame liner 204 is arranged between the user and the frame 202, and has portions 204a, 204b that extend along the frame 202, and may have a periphery that extends beyond the periphery of the frame 202. Particularly, an extending portion 204a extends downwardly from the frame 202 to a seam 206 whereat an upper segment 207 of the suspension element 201 extends from a base portion 208.

The surface area of the base portion 208 may extend over a substantial portion of a user's anatomy to better distribute forces incurred by the tensioning mechanism. The material forming at least the base portion 208 may have inherent compressibility, over such as a conventional strap, to offer cushioning over the user's anatomy. The concept of the larger surface area of the base portion may be similar to the foregoing embodiments according to FIG. 1.

The extending portion 204a and the upper segment 207 may be continuously formed such that there is no seam, whereby the frame liner 204 and suspension element 201 are formed in a unitary structure. The unitary structure may be formed from unbroken loop textile material, three-dimensional spacer material or a polymeric material, such as EVA. However, the unitary structure may be formed from different material, such as different segments being secured to one another (i.e., the extending portion 204a being of an EVA material or three-dimensional spacer material, and the suspension element 201 is an unbroken loop textile material).

Other suitable materials may be suitable for providing a suspension element 201 and a frame liner 204 that provide controlled movement of the suspension element 201 relative to the frame 202. In certain embodiments, the frame liner 204 is stationary relative to the frame 202, and the suspension element 201 is movably or pivotably attached to the frame liner 204 such that the suspension element 201 moves relative to the frame 202 and the frame liner 204.

The shape of the extending portion 204a may taper in width as it approaches the upper segment 207 to reduce coverage over a user's anatomy, and facilitate movement of the suspension element 201 toward the user. At least one attachment segment 169 may secure to the suspension element 201 by suitable means, such as stitching or an adhesive. Alternatively, or in addition to, the upper segment 207 may taper in width as it approaches the extending portion 204a, thereby forming an hourglass-like geometry. The tapering width of the extending portion 204a and/or the upper segment 207 may provide for controlled movement of the suspension element 201 relative to the frame 200.

The shape or geometry of the suspension element 201 may determine whether the suspension element 201 and any components suspended therefrom (if any) may move relative to the frame 202, whether proximally/distally, medially/laterally, or anteriorly/posteriorly. In the depicted embodiment, the tapering of the extending portion 204a coupled with the shape of the upper segment 207 may define a particular geometry suitable for the intended movement of the base 208 and the brace component 104 relative to the frame 202. In the depicted embodiment, the geometry of the connection between the upper segment 207 and the extending portion 204a is an hourglass shape, but other geometries are contemplated.

The extending portion 204a centers the suspension element 201 relative to the frame 202 and a user's anatomy along axis C. While in the illustration of FIG. 11, the extending portion 204a centers the suspension element 201, it may position the suspension element 201 in other configurations relative to the frame 202, such as offset from a center axis, particularly as required by a shape of the anatomy, which may be dynamic during use.

The suspension element 201 is arranged to position the brace component 104 at a relative position on a user's leg. The length of the extending portion 204a and the upper segment 207 axially position the brace component 104 a first distance D1, which may be predetermined, along a user's leg from a periphery of the frame 202, as in a lower periphery of the frame 202 in view of the depiction in FIG. 11. The base portion 208 of the suspension element 201 extends axially a second distance D2, which may be predetermined, from the first distance D1.

The suspension element 201, including the extending portion 204a, may be substantially inelastic to assure that the first and second distances D1, D2 remain constant. The suspension element 201 may be anisotropic so that is it elastic in a first direction, such as laterally L1 (i.e., extending between lateral and medial sides of the orthopedic device) or longitudinally L2 (i.e., length of leg or longitudinal axis of the leg). The elasticity may vary relative to lateral L1 and longitudinal L2 directions, such that elasticity in one direction is more than elasticity in another direction.

Figure 12:
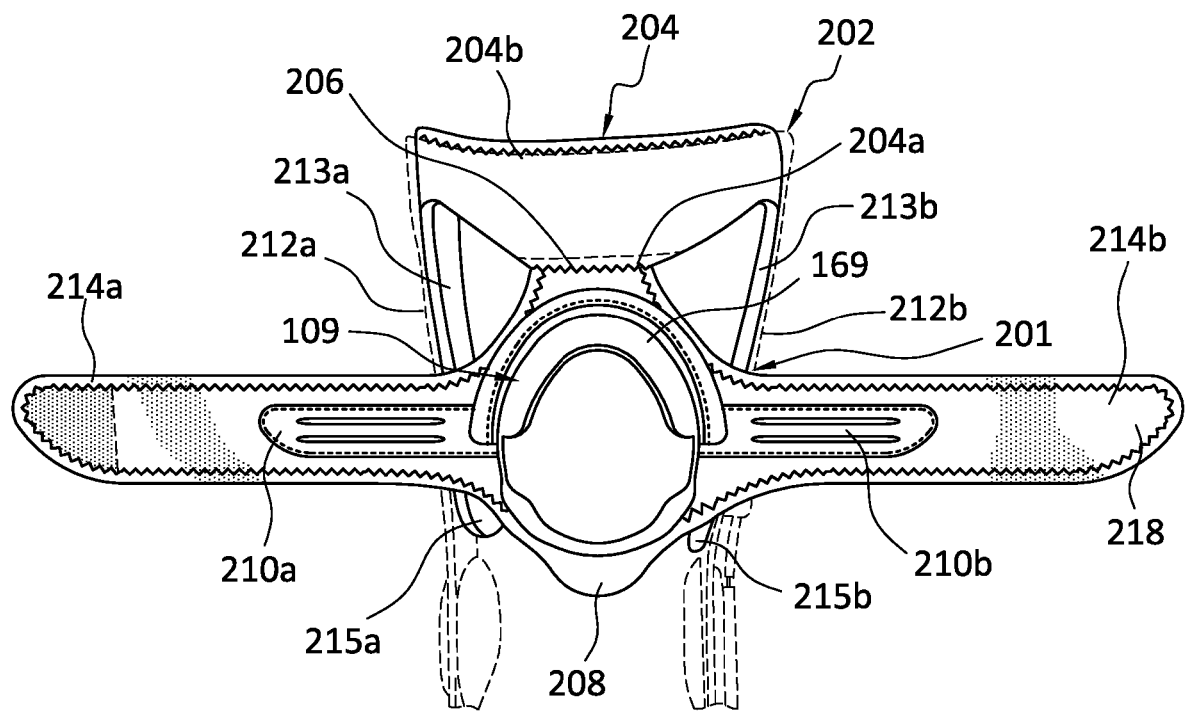
FIG. 12 is an elevational view showing schematically the suspension element of FIG. 11 in an open configuration from a perspective of a frontal view of the orthopedic device.
Figure 13:
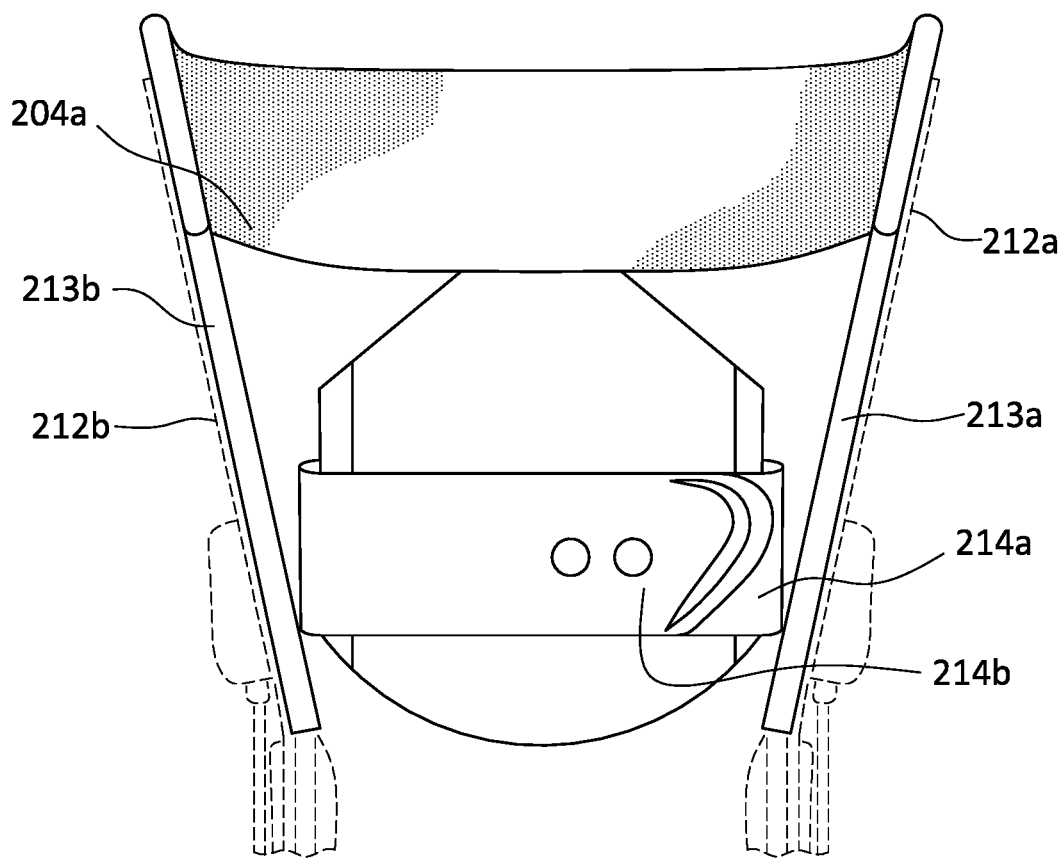
FIG. 13 is an elevational view showing schematically the suspension element of FIG. 11 in a closed configuration from a perspective of a rear view of the orthopedic device.

Referring to FIGS. 11-13, the suspension element 201 is unitary with the frame liner 204, as they form a continuous structure. The suspension element 201 tethers from the frame liner 204 and extends from the frame 202. As such the suspension element 201 can articulate relative to the frame 202, such as inwardly toward the user, or outwardly away from the user. The suspension element 201 includes first and second strap portions 214a, 214b extending from opposed sides thereof, e.g. medial and lateral sides, and are adapted to circumferentially extend about a user's anatomy with the base portion 208 to form a continuous or circumferential loop. The circumferential loop preferably extends within opposed first and second struts 212a, 212b of the frame 202, but independently secures to a user's anatomy between the opposed struts 212a, 212b. The circumferential loop allows for the brace component 104 to be located and function generally independently from the frame 202 aside from being suspended or tethered from the frame, as the struts 212a, 212b do not interfere with the functioning of the brace component 104. As regards "circumferential loop," a complete circumscription of the user's anatomy, e.g. a thigh, is affected by the circumferential loop.

In particular, as the first and second strap portions 214a, 214b form a circumferential loop surrounding the user's anatomy, the brace component 104 is supported directly on and in close engagement with the user's anatomy while being allowed to pivot in a direction about the attachment between the suspension element 201 and the frame liner 204. In the depicted embodiment, the brace component 104 is a dynamic tensioning system and the suspension element 201 may pivot anteriorly and posteriorly relative to the frame 202, particular during gait or as the dynamic tensioning system 104 is tensioned. The pivoting arrangement of the suspension element 201 and the independent straps 214a, 214b allow an off-the-shelf orthopedic device 200 to more closely fit the anatomy and needs of a particular user, as different users may require different degrees of tension in the dynamic tensioning system and may have differently sized anatomy.

The pivoting arrangement also allows the orthopedic device 200 to have greater effectiveness as the brace component can move to an advantaged location in a controlled manner independent of movement of the frame 202 of the orthopedic device 200. As regards to the "controlled manner," the suspension element 201 is arranged to allow the brace component 104 to move or pivot relative to the frame 202 only in desired directions and to desired degrees. In the depicted embodiment, the attachment between the suspension element 201 and the frame liner 204 forms a seam that allows for movement in anterior and posterior directions relative to the frame 202, while comparatively limiting medial/lateral and proximal/distal movements. In other embodiments, the suspension liner 201 may be arranged to promote medial/lateral and/or proximal/distal movements relative to anterior/posterior movements.

The frame liner 204 preferably has first and second extensions 213a, 213b that line the opposed first and second struts 212a, 212b, and extend to first and second end portions 215a, 215b, thereby providing greater comfort to a user and enhanced engagement between the frame 202 and the frame liner 204. The first and second straps 214a, 214b are arranged to form a circumferential loop independent of the first and second extensions 213a, 213b. The circumferential loop is arranged to adapt to asymmetrical anatomy of a user due to its flexibility and is arranged without interference from the frame or other brace components.

The second strap portion 214b has a tab 218 configured to engage the first strap portion 214a and secure therewith. Reinforcing sections 210a, 210b, similar to the covering 156 in FIG. 9, may extend from the cradle 109 and secure over the first and second strap portions 214a, 214b to reinforce the first and second strap portions 214a, 214b, particularly when cable segments extend thereover. As with the cradle 109, the reinforcing sections 210a, 210b are preferably formed from a more resilient material or tougher material than the material used to form the first and second strap portions 214a, 214b. The reinforcing sections 210a, 210b may be formed from a polymeric material whereas the strap portions 214a, 214b may be formed from an unbroken loop material, however any suitable material may be used.

In an alternative embodiment, the suspension element, including the first and second strap portions 214a, 214b, may be configured without a brace component. Rather, the first and second strap portions 214a, 214b may be arranged to form a circumferential loop around the user's anatomy that can pivot or move independent from the frame 202. In certain embodiments, the circumferential loop may offer compression to a desired portion of the anatomy, such as an injured muscle group, or the circumferential loop may provide that forces may be transmitted only in certain directions between the circumferential loop and the frame 202. Further, the suspension element according to FIG. 1 and accompanying description may be provided with the first and second strap portion as described above so as to form a continuous loop.

The orthopedic device having any of the embodiments of the suspension element of the disclosure advantageously solves the problem of existing orthopedic devices not properly suspending or supporting brace components over certain parts of a user's anatomy, which leads to existing devices causing discomfort and sub-optimal effectiveness. By providing a suspension element, a brace component may be suspended or supported over a user's anatomy with flexibility to adapt to a user's changing dimensions in particular directions while retaining a position in another direction.

The suspension element may comprise anisotropic materials or properties to provide different properties in different directions as dictated by a user's anatomy. In other embodiments the suspension element may comprise a circumferential loop independent of the frame of the orthopedic device, allowing for pivoting of a brace component supported on the suspension element independent of the frame, while being capable of suspending a brace component and articulating relative to the frame. This is accomplished while retaining improving breathability and cost-effectiveness.

While the foregoing embodiments have been described and shown, alternatives and modifications of these embodiments, such as those suggested by others, may be made to fall within the scope of the invention. While the orthopedic device having a suspension element has been described in a knee brace, it will be understood that the principles described may be extended to other types of orthopedic devices. It is to be understood that not necessarily all objects or advantages may be achieved under any embodiment of the disclosure. Those skilled in the art will recognize that the orthopedic device having a suspension element may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. The suspension element may be configured in combination with the features of both anisotropic properties and geometry to achieve the articulation in a controlled manner, and/or straps to form a circumferential loop.

In addition to the variations described herein, other known equivalents for each feature can be mixed and matched by one of ordinary skill in this art to construct an orthopedic device having a suspension element in accordance with principles of the present disclosure. It will be understood by the skilled artisan that the features described herein may be adapted to other types of orthopedic devices. Hence this disclosure and the embodiments and variations thereof are not limited to knee braces, but can be utilized in any orthopedic devices, as well as prosthetic and medical devices.

Although this disclosure describes certain exemplary embodiments and examples of an orthopedic device, it nevertheless will be understood by those skilled in the art that the present disclosure extends beyond the specifically disclosed knee brace embodiments to other alternative embodiments and/or uses of the disclosure and obvious modifications and equivalents thereof. It is intended that the scope of the present disclosure should not be limited by the particular disclosed embodiments described above, and may be extended to orthopedic devices and supports, and other applications that may employ the features described herein.

The invention claimed is:

1. An orthopedic device, comprising:
   a frame;
   a brace component; and
   a suspension element supporting the brace component and connecting the brace component to the frame, the suspension element being suspended relative to the frame and capable of movement relative thereto in a controlled manner;
   a retainer secured to the suspension element and adapted to hold the brace component, wherein the retainer is arranged with at least one securing feature having resilient properties and adapted to removably hold the brace component;
   wherein the suspension element is a flexible sheet having a plurality of openings.

2. The orthopedic device of claim 1, wherein the suspension element extends from a frame liner extending along a portion of the frame, the suspension element positioned outside of a periphery of the frame and moveable relative thereto, such that the frame liner extends stationary relative to the suspension element.

3. The orthopedic device of claim 1, wherein the retainer has a contoured profile along an outer surface thereof arranged to correspond to anatomical geometry along which the retainer is adapted to abut.

4. The orthopedic device of claim 1, wherein the retainer is formed from a closed-cell EVA foam.

5. The orthopedic device of claim 1, wherein the suspension element has a geometry arranged to provide movement of the suspension element in the controlled manner relative to the frame.

6. The orthopedic device of claim 5, wherein the geometry of the suspension element includes a tapering portion extending between the brace component and the frame, the tapering portion arranged to facilitate pivoting movement of the brace component generally along a longitudinal axis of the orthopedic device.

7. An orthopedic device, comprising:
   a frame;
   a brace component; and
   a suspension element supporting the brace component and connecting the brace component to the frame, the suspension element being suspended relative to the frame and capable of movement relative thereto in a controlled manner;
   a retainer secured to the suspension element and adapted to hold the brace component, wherein the retainer is arranged with at least one securing feature having resilient properties and adapted to removably hold the brace component;
   wherein the brace component is a tensioning mechanism having at least one cable extending therefrom.

8. An orthopedic device, comprising:
   a frame;
   a brace component; and
   a suspension element supporting the brace component and connecting the brace component to the frame, the suspension element being suspended relative to the frame and capable of movement relative thereto in a controlled manner;
   wherein the brace component is a tensioning mechanism having at least one cable extending therefrom;
   wherein the at least one cable connects to the frame and extends to the frame from the suspension element and extends along a length of the frame to secure a first end of the at least one cable to the frame, the at least one cable movable relative to the suspension element and the frame.

9. An orthopedic device, comprising:
   a frame;
   a brace component; and
   a suspension element supporting the brace component and connecting the brace component to the frame, the suspension element being suspended relative to the frame and capable of movement relative thereto in a controlled manner;
   wherein the suspension element has a geometry arranged to provide movement of the suspension element in a controlled manner relative to the frame;
   wherein the suspension element extends from a frame liner extending along a portion of the frame, the suspension element positioned outside of a periphery of the frame and moveable relative thereto, such that the frame liner extends stationary relative to the suspension element;
   wherein the suspension element forms a circumferential loop extending and arranged to tension independently from the frame, the circumferential loop extending within a space defined by portions of the frame, the circumferential loop extending generally in a direction opposite to a direction from which the suspension element is suspended relative to the frame;
   wherein the circumferential loop is defined at least in part by a base portion of the suspension element and first and second straps extending from the base portion and adapted to secure to one another.

10. An orthopedic device, comprising:
    a frame;
    a brace component; and
    a suspension element supporting the brace component and connecting the brace component to the frame, the suspension element being suspended relative to the frame and capable of movement relative thereto in a controlled manner;
    wherein the suspension element forms a circumferential loop extending and arranged to tension independently from the frame;
    wherein the circumferential loop extends within a space defined by portions of the frame, the circumferential loop extending generally in a direction opposite to a direction from which the suspension element is suspended relative to the frame;
    wherein the circumferential loop is defined at least in part by a base portion of the suspension element and first and second straps extending from the base portion and adapted to secure to one another.

11. The orthopedic device of claim 10, further comprising first and second reinforcing sections overlying the first and second straps, respectively, and extending parallel to a length of the first and second straps, the first and second reinforcing sections having greater stiffness than the first and second straps.

12. The orthopedic device of claim 10, wherein the suspension element is generally flexible and inelastic inclusive of the first and second straps and the base portion, and the suspension element.

13. An orthopedic device, comprising:
a frame;
a brace component; and
a suspension element supporting the brace component and connecting the brace component to the frame, the suspension element being suspended relative to the frame and capable of movement relative thereto in a controlled manner, the suspension element having a geometry arranged to provide movement of the suspension element in a controlled manner relative to the frame;
a retainer secured to the suspension element and adapted to hold the brace component and arranged with at least one securing feature having resilient properties and adapted to removably hold the brace component, the retainer having a contoured profile along an outer surface thereof arranged to correspond to anatomical geometry along which the retainer is adapted to abut;
wherein the brace component is a tensioning mechanism having at least one cable extending therefrom, the at least one cable connecting to the frame and extending to the frame from the suspension element and along a length of the frame to secure a first end of the at least one cable to the frame, the at least one cable movable relative to the suspension element and the frame.

\* \* \* \* \*